United States Patent
Fermigier et al.

(12) 
(10) Patent No.: US 6,533,416 B1
(45) Date of Patent: Mar. 18, 2003

(54) CONTACT OR INTRAOCULAR LENS AND METHOD FOR ITS PREPARATION

(75) Inventors: Bruno Fermigier, Paris (FR); Richard Legras, Robinson (FR); Nicolas Chateau, Paris (FR)

(73) Assignee: Ocular Sciences, Inc., Concord, CA (US)

( * ) Notice: Subject to any disclaimer, the term of this patent is extended or adjusted under 35 U.S.C. 154(b) by 0 days.

(21) Appl. No.: 09/910,491

(22) Filed: Jul. 20, 2001

(51) Int. Cl.$^7$ ............................. G02C 7/04; A61F 2/16
(52) U.S. Cl. .................. 351/160 R; 351/161; 351/177; 623/6.27
(58) Field of Search .................... 351/160 R, 160 H, 351/161, 162, 177; 623/6.27

(56) References Cited

U.S. PATENT DOCUMENTS

| | | | |
|---|---|---|---|
| 4,095,878 A | 6/1978 | Fanti | 351/161 |
| 4,324,461 A | 4/1982 | Salvatori | 351/161 |
| 5,220,359 A | 6/1993 | Roffman | 351/160 R |
| 5,570,143 A | 10/1996 | Newman | 351/160 R |
| 5,652,638 A | 7/1997 | Roffman et al. | 351/161 |
| 5,760,870 A * | 6/1998 | Payor et al. | 351/161 |
| 5,796,462 A | 8/1998 | Roffman et al. | |
| 5,971,541 A | 10/1999 | Danker et al. | 351/160 R |
| 6,139,147 A * | 10/2000 | Zhang | 351/161 |

FOREIGN PATENT DOCUMENTS

| | | |
|---|---|---|
| EP | 0949529 | 10/1999 |
| FR | 2760853 | 9/1998 |

OTHER PUBLICATIONS

M. Born, E. Wolf, Principles of Optics, 6th Ed., Pergamon Press, pp. 480–490 (1980).
P. Mouroulis, X. Cheng, Optical Engineering, vol. 33, No. 8, pp. 2626–2631 (1994).
D. Atchison, "Subjective Depth–to–Focus of the Eye", Optometry and Vision Science, vol. 74, No. 7 (1997).

* cited by examiner

Primary Examiner—Scott J. Sugarman
(74) Attorney, Agent, or Firm—Stout, Uxa, Buyan & Mullins, LLP; Frank J. Uxa

(57) ABSTRACT

Toric contact or intraocular lenses having a correcting portion characterized by one or more novel constructions that each produce an optical path that improves angular misalignment tolerance. The lens may be constructed with a "smooth atoric" aspect where the optical path through the correcting portion of the lens corrects for both astigmatism and an axisymmetric aberration other than astigmatism, there being no sudden surface discontinuity between the regions that provide the different corrections (thus, "smooth"). In another embodiment, the lens may be constructed with so-called "sectors" circumferentially arranged around the optical axis such that an optical path through the correcting portion of the lens varies as a function of the angular separation from the reference meridian plane, and the correcting portion is divided into at least two sectors having different astigmatism correction axes. In either embodiment, the correcting surface may be provided on either or both of the anterior or posterior faces of the lens, and the optical performance of the lens in case of angular displacement (the "angular misalignment tolerance") is increased. Specifically, the angular misalignment tolerance is increased by at least 30% over a standard toric lens of the same class. Definition of the particular shape of the lens enables a mold die of that shape to be formed, or lens machining tools may be used.

41 Claims, 5 Drawing Sheets

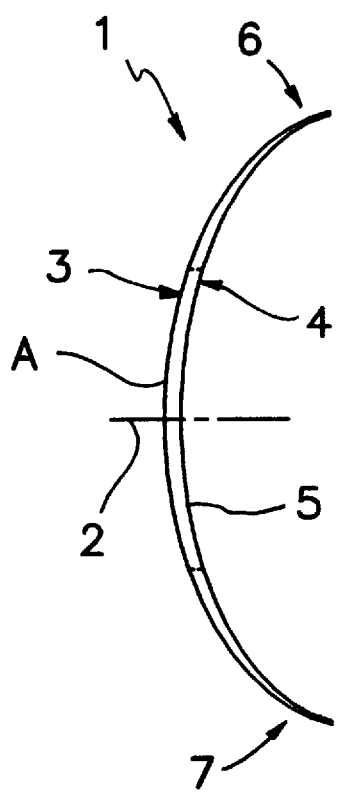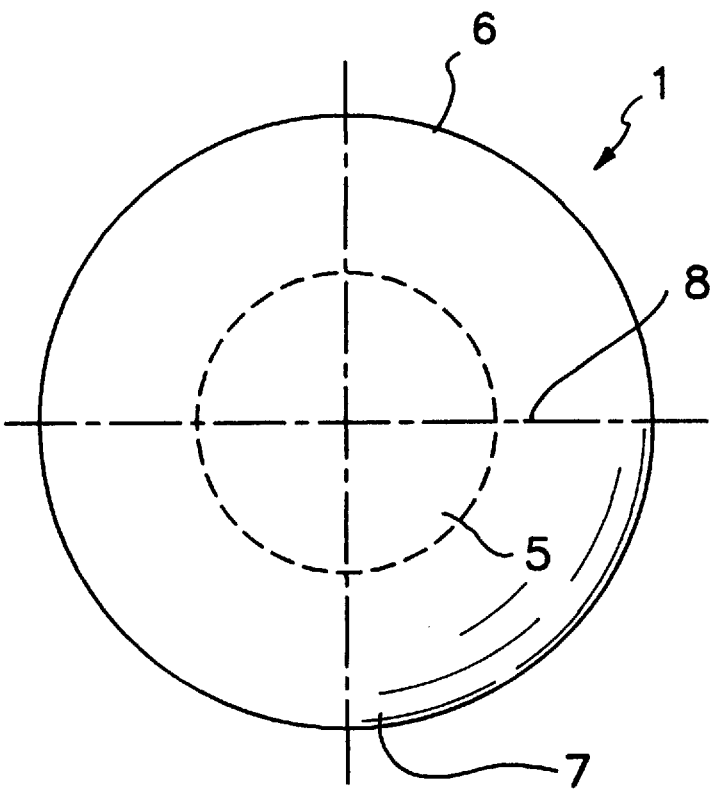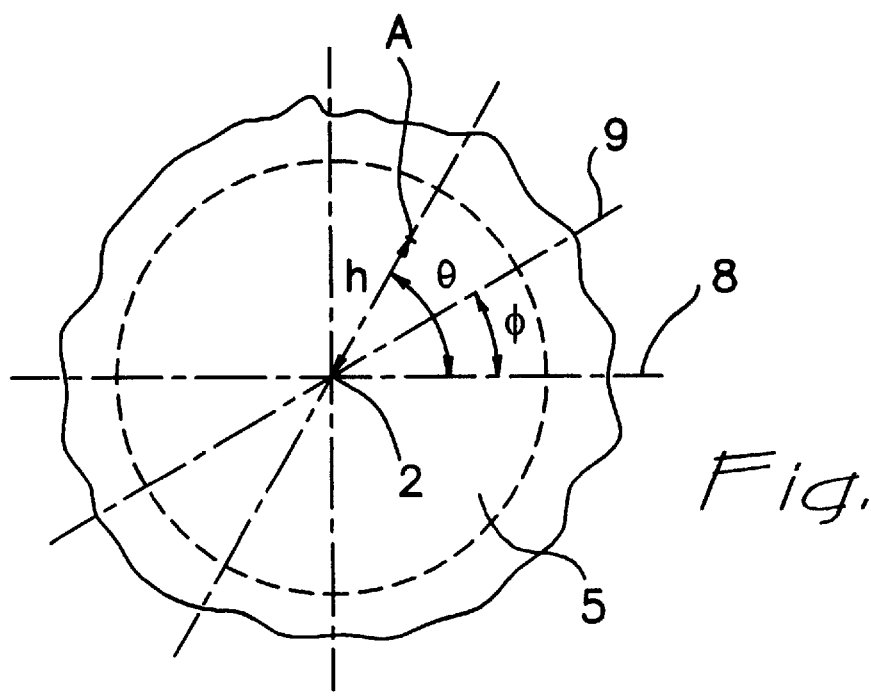

CONTACT OR INTRAOCULAR LENS AND METHOD FOR ITS PREPARATION

BACKGROUND OF THE INVENTION

The invention relates to contact or intraocular lenses to correct the vision resulting from a possibly myopic or hyperopic and/or possibly presbyopic astigmatic eye.

It is known that myopia or hyperopia is generally corrected thanks to a spherical surface whose center of curvature must be on the optical axis of the lens, where the parameter that is usually used to define the correction to be made is the introduced spherical optical power, generally called "sphere value."

It is also known that the correction of presbyopia is advantageously obtained thanks to a complex surface which procures a progressive simultaneous vision correction, that is a correction whose spherical optical power varies delicately (and not abruptly) between the center and the periphery of the correcting zone, so that several images are simultaneously formed on the retina, the useful image being selected as a result of sorting by the cortex.

It is also known that the correction of astigmatism is generally obtained thanks to a toric surface whose symmetrical plane must be oriented along a meridian plane of the eye to be corrected, that is along a plane which contains the optical axis of this eye, where the parameters that are usually used to define the correction to be made are, on the one hand, the angular separation between the meridian plane along which the toric surface must be oriented and the reference meridian plane, corresponding to the horizontal meridian plane when the wearer of the lens is standing, this angular difference usually referred to as "the axis" of the correction, and, on the other hand, by the cylindrical optical power introduced, usually called "cylinder value."

For the toric surface of a contact lens to remain correctly positioned with regard to the eye, a means for the angular stabilization of the lens with respect to the eye must be provided, and, notably, a ballast prism which makes it possible to maintain the lens in position thanks to the weight, or bosses as described in French Patent No. 2,760,853, which use the dynamic effect produced by blinking the eyelids so that the lens remains permanently correctly positioned, or once again a progressive thinning or lightening at the top and bottom of the lens can be provided, along a direction which must correspond to the vertical direction of the eye, as described in U.S. Pat. No. 4,095,878, or a stabilization means which comprises a ballast and lightening at the top part of the lens, as described in U.S. Pat. No. 4,324,461. All these stabilization means, with the exception of the ballast prism, are located outside of the correcting portion of the contact lens, being located in the center of the lens at the level of the pupil of the eye to be corrected, for example, inside a circle having a radius of 4 mm centered about the optical axis of the lens.

Each one of these means for angular stabilization yields good results, the contact lens remaining, overall, correctly oriented. However, while the different orientations successfully assumed by the lens over time have a mean value which corresponds to the desired value, the amplitude of the variations in orientation around this mean value is such that at times the angular displacement produces a significant degradation of the optical performances.

Such a problem with angular stabilization does not arise with intraocular lenses, which are made in the form of an internal implant in the eye equipped with holding hooks which project radially but can nevertheless produce an angular displacement with regard to the nominal position during placement of the implant.

In order to correct the angular displacement, U.S. Pat. No. 5,570,143 proposes to apply to the toric lenses the techniques that are usually used to prevent spherical aberrations, techniques which have the effect of improving the depth of field where the proposed toric lens presents over at least one surface an optical topography which induces an effect of depth of field having a spherical power which would be sufficiently high to correct for the optical effect of the angular positioning separation.

U.S. Pat. No. 5,652,638 proposes a similar solution, except that the traditional techniques for improving depth of field are replaced by concentric rings.

U.S. Pat. No. 5,796,462 proposes to obtain the effect of depth of field thanks to a lens in which one of the surfaces is of the toric type, in which the meridians are not circles but curves belonging to the family of the classic cone shapes used to prevent spherical aberrations. The other face of the lens is spherical or has concentric rings.

SUMMARY OF THE INVENTION

The present invention is intended to reduce the effects of the angular displacement on toric contact or intraocular lenses by provision of a correcting portion characterized by one or more novel constructions. Per convention, the expression "optical path" designates the difference in optical path introduced by a lens on the rays originating from a point light source located at infinity on the optical axis.

In one embodiment, the lens may be constructed with a "smooth atoric" aspect where the optical path through the correcting portion of the lens corrects for both astigmatism and an axisymmetric aberration other than astigmatism, there being no sudden surface discontinuity (thus, "smooth"). In another embodiment, the lens may be constructed with so-called "sectors" circumferentially arranged around the optical axis such that an optical path through the correcting portion of the lens varies as a function of the angular separation from the reference meridian plane, and the correcting portion is divided into at least two sectors having different astigmatism correction axes. In either embodiment, the correcting surface may be provided on either or both of the anterior or posterior faces of the lens, and the optical performance of the lens in case of angular displacement (the "angular misalignment tolerance") is increased. Specifically, the angular misalignment tolerance is increased by at least 30% over a standard toric lens of the same class and in the same conditions (i.e., the same cylinder and pupil diameter).

The contact or intraocular lenses of the present invention are best described by the desired optical path through the correcting portion, and it will be understood by those of skill in the art that there are a number of ways to construct the correcting portion so as to produce such an optical path. For example, definition of the particular shape of the lens enables a mold die of that shape to be formed. Lens machining tools may also be used. Whatever the method of manufacture, the present invention is intended to encompass lenses formed to have a particular optical path.

For this purpose, the present invention provides a contact or intraocular lens comprising a correcting portion to correct the vision of a possibly myopic or hyperopic and/or possibly presbyopic astigmatic eye, comprising an optical axis and a reference meridian; characterized in that it introduces, for correction of only the astigmatism, an optical path varying as a function of the distance with regard to the optical axis and as a function of the angular separation with regard to the reference meridian, at least when this distance is between 0.4 mm and 2.4 mm, according to the following equation:

$$\delta_A(h,\theta)=\delta_{toric}(h,\theta)+\delta_{atoric}(h,\theta)$$

in which equation:

$\delta_{toric}(h,\theta)$ is a cylindrical optical path which satisfies, according to the parabolic approximation, the expression $\delta_{toric}(h,\theta)=C/2\ h^2\ \sin^2(\theta-\phi)$, where $\phi$ is the axis required to correct the astigmatism of said eye expressed as an angular separation with regard to said reference meridian, and where C is the cylinder value required to correct the astigmatism of said eye; and $\delta_{atoric}(h,\theta)$ is an optical path, such that, when h is a constant, it varies as a function of $\theta$ with a $2\pi$ period, and differently from $\sin^2(\theta-\phi)$ where this optical path in addition satisfies the condition:

$$\Delta\phi' \geq 1.3\Delta\phi$$

which expresses the 30% increased "angular misalignment tolerance," and in which in equation:

$\Delta\phi$ is the amplitude of the range of variation $[-\frac{1}{2}\Delta\phi, \frac{1}{2}\Delta\phi]$ of a variable x, which amplitude is such that, for any value of x in this interval, the following condition proves correct:

$$MTFa[\delta_{toric}(h,\theta-x)-\delta_{toric}(h,\theta)] \geq MTFa[0.25h^2/2]$$

$\Delta\phi'$ is the amplitude of the range of variation $[-\frac{1}{2}\Delta\phi', \frac{1}{2}\Delta\phi']$ of a variable x, which amplitude is such that, for any value in this interval, the following condition proves correct:

$$MTFa[\delta_A(h,\theta-x)-\delta_{toric}(h,\theta)] \geq MTFa[0.25h^2/2]$$

The notation MTFa[f(h,$\theta$)] designating, for an optical path f(h,$\theta$), the calculated optical quality criteria arising from the modulation transfer function produced by this optical path, for a predetermined pupil diameter, between 4 and 7 mm, according to the formula:

$$MTFa[f(h,\theta)] = \int_{\nu=5}^{\nu=15}\int_{\chi=0}^{\chi=360}\frac{MTF}{360}[f(h,\theta)](\nu,\chi)\partial\nu\partial\chi$$

in which formula $\nu$ and $\chi$ are the polar coordinates in the plane of the angular frequencies, $\nu$ being expressed in cycles per degree and $\chi$ in degrees; and in which MTF[f(h,$\theta$)]($\nu,\chi$) is the modulation transfer function of the optical path f(h,$\theta$) according to said polar coordinates.

Again, the expression "optical path" used above, and more generally in the present specification, more specifically designates the difference in optical path introduced by a lens on the rays originating from a point light source located at infinity on the optical axis, so that the phase shift $\psi$ introduced by this lens is connected to the optical path $\delta$, in the sense of the present specification, by the relationship:

$$\psi = 2\pi\delta/\lambda$$

where $\lambda$ is the wavelength of the light rays, the negative values of $\delta$ and $\psi$ correspond to a delay introduced on the optical wave, and the positive values to an advance.

Naturally, this optical path is valid for wavelengths located in the visible light range, and notably for the reference wavelength $550\times10^{-9}$ m.

In practice, $\psi(h,\theta)$, and more generally the phase shift or the optical path introduced by the lens can be determined by interferometry or by another method for measuring the optical phase shift, or they can be derived from the analysis of the wave front originating from the lens, realized by means of a Shack-Hartmann analyzer or another type of wave front analyzer.

The modulation transfer function, MTF, can be calculated from the phase shift or the optical path for a given pupil size according to well known algorithms (reference: M. Born, E. Wolf, Principles of Optics, Sixth Edition, Ed. Pergamon Press, p. 480 (1980)). MTFa, calculated by integration of MTF according to the formula indicated above, is a numerical criterion which allows the characterization of the performances of an optical system in good correlation with the subjective quality of the images produced by this system (reference: P. Z. Mouroulis, X. Cheng, Optical Engineering) 33:2626–2631, 1994).

It should be noted that the term $0.25\ h^2/2$ corresponds to a defocusing of 0.25 diopter (D). The MTFa threshold appearing above is chosen as the value obtained when one considers a pure spherical defect of 0.25 D. It is assumed that a defocusing of 0.25 D with a 6 mm lens is just detectable by the wearer (D. A. Atchison et al., Subjective depth-of-focus of the eye, Optom. Vis. Sci. 74:511–520, 1997). The corresponding value of MTFa is thus chosen as minimum acceptable value. According to the invention, this threshold allows the definition of the acceptable angular tolerance of a lens intended for correcting astigmatism.

It should be noted that in each one of the above-mentioned U.S. Pat. Nos. 5,570,143, 5,652,638 and 5,796,462, the modification proposed with regard to classic toric lens concerns the radial dependence of the shape of one of the surfaces, that is the dependence according to the variable h, while the present invention proposes to work on the angular dependence (variable $\theta$), alone, or in combination with the radial dependence.

More specifically, the modification with regard to a classic toric lens, which modification is represented by $\delta_{atoric}$, such that, when h remains constant and $\theta$ varies, $\delta_{atoric}(h,\theta)$ does not remain constant, but fluctuates with a periodicity in $\theta$ of $360°$ ($2\pi$), differently from $\sin^2(\theta-\phi)$ Thus, in the lens according to the invention, the nonaxisymmetric component is not exclusively toric.

In addition, it should be noted that each of the U.S. Pat. Nos. 5,570,143, 5,652,638 and 5,796,462, quantifies the modification made with regard to a conventional toric lens solely on the basis of optical powers.

In contrast, according to the present invention, the modification effected with regard to a classic toric lens is not evaluated on the basis of an optical power criterion, but on the basis of the optic quality criterion represented by MTFa.

It should be noted that until now MTFa was used for optical instruments, and not for the system formed by the eye and by a lens.

According to a first preferred embodiment, the term $\delta_A(h,\theta)$ satisfies the equation:

$$\delta_A(h,\theta) = \sum_{i\in N}\beta_i(h)\cos[i(\theta-\phi)]$$

in which equation:

N is the set of whole numbers; and $\beta_i(h)$ is a set of functions satisfying the following condition:

$$\sum_{i\in N'} \left[ \left( \frac{1}{h_{\max} - h_{\min}} \int_{h_{\min}}^{h_{\max}} \frac{2\beta_i(h)}{h^2} dh \right)^2 \right] \geq 0.005 \text{ m}^{-2}$$

in which equation N' is equal to N excluding 0 and 2, while $h_{min}$ and $h_{max}$ are the minimum distance and the maximum distance, respectively, with regard to the optical axis of the zone of the correcting portion provided to correct the astigmatism.

It should be noted that $\delta_A(h,\theta)$ is thus expressed according to its Fourier series decomposition in cosine. In practice, this series is convergent, so that N can be likened to whole numbers from zero to several tens.

In the case where $\beta_i(h)$ is of the type $$\frac{h^2}{2}\alpha_i$$

it should be noted that if $\alpha_i$ is a constant, the term $$\frac{1}{h_{\max} - h_{\min}} \int_{h_{\min}}^{h_{\max}} \frac{2\beta_i(h)}{h^2} dh$$

corresponds to $\alpha_i$, whereas if $\alpha_i$ is not a constant the above term corresponds to the weighted mean value of $\alpha_i$ over the range of variation of h.

Given that the components of the function $\delta_A(h,\theta)$ for the indexes i=0 and i=2 jointly represent a correction of the spherocylindrical type, the fact that the sum of the squares of the mean coefficients $\alpha_i$ other than for i=0 and i=2 is different from 0, is characteristic of the fact that the correction provided by the lens according to the a invention comprises a nonaxisymmetric component obtained by a correction other than toric, that is atoric.

The value of 0.005 m$^{-2}$ for this sum corresponds to a minimal threshold, determined experimentally, and it is preferred to use values above this to obtain a significant optical effect.

In a structural shape preferred because of its simplicity, each of the functions $\beta_i(h)$ satisfies the equation:

$$\beta_i(h) = \frac{h^2}{2}\alpha_i$$

in which equation $\alpha_i$, for i∈N, is a constant coefficient.

It should be noted that, if the correction had been purely spherocylindrical, then $$\alpha_0 = P_{VL} + \frac{C}{2}$$

$$\alpha_2 = -\frac{C}{2}$$

where $P_{VL}$ is the sphere power.

In a first preferred example of this structural shape, the optical path $\delta_A(h,\theta)$ satisfies the equation:

$$\delta_A(h, \theta) = \frac{C+c}{2} h^2 \sin^2(\theta - \phi + \eta)$$

in which equation $\eta$ is equal to $\psi$ for $\theta-\phi$ between 0° and 180°, and equal to $-\psi$ for $\theta-\phi$ between 180° and 360°, c and $\psi$ being predetermined constants. This divides the lens into 180° "sectors" having different astigmatism correction axes.

More specifically, the correcting portion of the lens according to the invention is divided into two sectors separated by the reference meridian plane, the correction axis of one of the sectors being inclined with regard to a conventional toric lens, by the angle $\psi$, in a first direction, whereas the correction axis of the other sector is inclined from the angle $-\psi$ in the other direction.

Thus, for example, if one has an angular displacement of the lens of 5° with regard to its ideal position, and the angle $\psi$ is 8°, one of the sectors is separated by 3° from the ideal and the other sector by 13°.

It is possible, as will be seen below, to achieve the result that the overall image obtained on the retina by these two sectors is of better quality, conforming to the criterion MTFa, than that which one would have with the same angular displacement for a purely toric lens.

It should be noted that the best results are not obtained using the exact cylinder power C, but with a slightly different power equal to C+c.

It is preferred that, taking into account the good results obtained, the constants c and $\psi$ have, depending on the value of C, the values given by the table below, at ±0.125 diopter (D) for C+c, and at ±1° for $\psi$:

| C(D) | C + c(D) | $\psi$ |
|---|---|---|
| 3 | 3.00 | 6.3° |
| 2.5 | 2.48 | 7.6° |
| 2 | 2.04 | 9.1° |
| 1.5 | 1.49 | 12.7° |
| 1 | 1.00 | 19.1° |

These values are particularly suitable for a pupil diameter of 6 mm.

Preferably, for the same reasons, the constants c and $\psi$ have, depending on the value of C, the values given in the table below, at ±0.125 diopter (D) for C+c, and at

| C(D) | C + c(D) | $\psi$(°) |
|---|---|---|
| 3 | 2.99 | 4.7° |
| 2.5 | 2.50 | 5.7° |
| 2 | 1.98 | 7.2° |
| 1.5 | 1.49 | 9.5° |
| 1 | 0.99 | 14.4° |

These values are particularly suitable for a pupil diameter of 8 mm.

It is also preferred for the same reasons and conforming to an experimentally evident law, that constant c is equal to zero and constant $\psi$ takes on the value given by the formula below, to ±1°:

$$\psi = \frac{114}{C \cdot DP}$$

in which formula DP is the pupil diameter, expressed in millimeter (mm), $\psi$ being expressed in degrees (°) and C in diopters (D).

In an alternate preferred second example of this structural shape, the optical path $\delta_A(h,\theta)$ satisfies the equation:

$$\delta_A(h, \theta) = \frac{C+c}{2}h^2\sin^2(\theta - \phi + \eta)$$

in which equation η is equal to ψ for θ−φ between 0° and 90°, and for θ−φ between 180° and 270°, and equal to −ψ for θ−φ between 90° and 180°, and for θ−φ between 270° and 360°, c and ψ being predetermined constants.

Thus, the correcting portion of the lens according to the invention is divided into four sectors, separated by the reference meridian plane and by the meridian plane orthogonal to the latter plane, the correction axis of the sectors being alternately inclined, with regard to a conventional toric lens, by the angle ψ in a first direction and −ψ in the other direction.

Thus, it is possible to obtain, overall, on the retina, with these four sectors, an image of better quality, conforming to the criterion MTFa, than that which one would obtain for the same angular displacement with a purely toric lens.

As for the first preferred example disclosed above, the best results are not obtained with, very precisely, the cylinder power C, but with a slightly different power equal to C+c.

It should also be noted that the contact lens according to the present preferred example offers, with regard to the lens according to the preferred example with two opposite sectors disclosed above, the advantage of being less sensitive to decentering.

The centering errors in fact mutually compensate each other by the opposite sectors.

Preferably, taking into account the good results obtained, the constants c and ψ have, depending on the value of C, the values given in the table below, at ±0.125 diopter (D) for C+c at ±1° C. for ψ:

| C(D) | C + c(D) | ψ(°) |
|---|---|---|
| 3 | 2.98 | 5.0 |
| 2.5 | 2.47 | 6.1 |
| 2 | 2.00 | 7.4 |
| 1.5 | 1.47 | 10.5 |
| 1 | 0.95 | 16.7 |

These values are particularly suitable for a pupil diameter of 6 mm. same reasons, the constants c and ψ have, depending on the n in the table below, at ±0.125 diopter (D) for C+c, and at ±1° C. for ψ:

| C(D) | C + c(D) | ψ(°) |
|---|---|---|
| 3 | 3.00 | 3.6 |
| 2.5 | 2.48 | 4.5 |
| 2 | 1.98 | 5.7 |
| 1.5 | 1.49 | 7.5 |
| 1 | 0.97 | 12.0 |

These values are particularly suitable for a pupil diameter of 8 mm.

It is also preferred, for the same reasons, and according to an experimentally observed law, that the constant c is equal to zero and the constant ψ takes on the value given by the formula below to ±1°:

$$\psi = \frac{90}{C \cdot DP}$$

in which formula DP is the pupil diameter, expressed in millimeter (mm), ψ being expressed in degrees (°) and C in diopters (D).

In a second preferred embodiment, the term $\delta_A(h,\theta)$ satisfies the equation:

$$\delta_A(h, \theta) = \sum_{i \in E} \beta_i(h)\cos[i(\theta - \phi)]$$

in which equation:

E is a finite set comprising the whole numbers starting from 0; and $\beta_i(h)$ is a set of functions satisfying the following condition:

$$\sum_{i \in E'}\left[\left(\frac{1}{h_{max} - h_{min}}\int_{h_{min}}^{h_{max}}\frac{2\beta_i(h)}{h^2}dh\right)^2\right] \geq 0.005 \text{ m}^2$$

in which equation E' is equal to E disqualifying 0 and 2, while $h_{min}$ and $h_{max}$ are the minimum distance and the maximum distance, respectively, with regard to the optical axis of the zone [sic] of the correcting portion provided to correct the astigmatism.

In a first preferred structural shape of this second embodiment, because of its simplicity, each one of the functions $\beta_i(h)$ satisfies the equation:

$$\beta_i(h) = \frac{h^2}{2}\alpha_i$$

in which equation each $\alpha_i$, for i∈E is a constant coefficient.

This preferred structural shape notably corresponds to one of the examples with two or four sectors, disclosed above, with low pass filtering for the optical path, which consists in keeping only the first coefficients $\alpha_i$, for example, only up to i=10, or only up to i=3, and with an optimization of these coefficients.

Thus one prevents the existence, on the lens, of a crest between the sectors whose correction axis is differently inclined, which facilitates the manufacture of the lens and prevents wearer discomfort which could be produced by such a crest.

Preferably, because of the good results obtained based on a lens according to the first preferred example disclosed above, with two opposite sectors, the set E comprises the whole numbers from 0 to 10, and the coefficients $\alpha_i$ have, as a function of C, values such that they satisfy the inequation:

$$\sqrt{\sum_{i \in E}(\alpha_i - \alpha_i')^2} \leq 0.05 \text{ m}^{-1}$$

the coefficients $\alpha_i'$ having the values given in the table below:

| $C_{(D)}$ | $\alpha'_0$ | $\alpha'_1$ | $\alpha'_2$ | $\alpha'_3$ | $\alpha'_4$ | $\alpha'_5$ | $\alpha'_6$ | $\alpha'_7$ | $\alpha'_8$ | $\alpha'_9$ | $\alpha'_{10}$ |
|---|---|---|---|---|---|---|---|---|---|---|---|
| 3   | 1.521 | −0.289 | −1.450 | 0.168 | 0 | 0.040 | 0 | 0.019 | 0 | 0.011 | 0 |
| 2.5 | 1.277 | −0.284 | −1.200 | 0.168 | 0 | 0.041 | 0 | 0.019 | 0 | 0.011 | 0 |
| 2   | 1.034 | −0.299 | −0.942 | 0.165 | 0 | 0.048 | 0 | 0.022 | 0 | 0.010 | 0 |
| 1.5 | 0.775 | −0.273 | −0.661 | 0.163 | 0 | 0.040 | 0 | 0.018 | 0 | 0.011 | 0 |
| 1   | 0.522 | −0.261 | −0.383 | 0.157 | 0 | 0.038 | 0 | 0.018 | 0 | 0.010 | 0 |

These values are particularly suitable for a pupil diameter of 6 mm.

Preferably, for the same reasons, still based on a lens according to the first preferred example, disclosed above, with two opposite sectors, the set E comprises the whole numbers from 0 to 10, and the coefficients $\alpha_i'$ have, as a function of C, values such that they satisfy the inequation:

$$\sqrt{\sum_{i \in E}(\alpha_i - \alpha'_i)^2} \leq 0.05 \text{ m}^{-1}$$

the coefficients $\alpha_i'$ having the values given in the table below:

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3   | 1.502 | −0.216 | −1.465 | 0.127 | 0 | 0.031 | 0 | 0.014 | 0 | 0.008 | 0 |
| 2.5 | 1.261 | −0.218 | −1.215 | 0.126 | 0 | 0.030 | 0 | 0.014 | 0 | 0.008 | 0 |
| 2   | 1.015 | −0.214 | −0.964 | 0.127 | 0 | 0.031 | 0 | 0.014 | 0 | 0.008 | 0 |
| 1.5 | 0.766 | −0.212 | −0.695 | 0.124 | 0 | 0.030 | 0 | 0.014 | 0 | 0.008 | 0 |
| 1   | 0.516 | −0.203 | −0.425 | 0.121 | 0 | 0.030 | 0 | 0.014 | 0 | 0.008 | 0 |

These values are particularly suitable for a pupil diameter of 8 mm.

It is also preferred, based on a lens according to the second preferred example disclosed above, with four sectors, that the set E comprises the whole numbers from 0 to 10, and the coefficients $\alpha_i$ have, as a function of C, values such that they satisfy the inequation:

$$\sqrt{\sum_{i \in E}(\alpha_i - \alpha'_i)^2} \leq 0.05 \text{ m}^{-1}$$

the coefficients $\alpha_i'$ having the values given in the table below:

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3   | 1.331 | 0 | −1.472 | 0 | 0.114 | 0 | 0 | 0 | 0.023 | 0 | 0 |
| 2.5 | 1.071 | 0 | −1.206 | 0 | 0.107 | 0 | 0 | 0 | 0.024 | 0 | 0 |
| 2   | 1.830 | 0 | −0.940 | 0 | 0.112 | 0 | 0 | 0 | 0.023 | 0 | 0 |
| 1.5 | 0.575 | 0 | −0.667 | 0 | 0.108 | 0 | 0 | 0 | 0.024 | 0 | 0 |
| 1   | 0.332 | 0 | −0.384 | 0 | 0.105 | 0 | 0 | 0 | 0.025 | 0 | 0 |

These values are particularly well suited for a pupil diameter of 6 mm.

Preferably, for the same reasons, still based on a lens according to the second preferred example disclosed above, with four sectors, the set E comprises the whole numbers from 0 to 10, and the coefficients $\alpha_i$ have, as a function of C, values such that they satisfy the inequation:

$$\sqrt{\sum_{i \in E}(\alpha_i - \alpha'_i)^2} \leq 0.05 \text{ m}^{-1}$$

the coefficients $\alpha_i'$ having the values given in the table below:

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3   | 1.365 | 0 | −1.471 | 0 | 0.081 | 0 | 0 | 0 | 0.016 | 0 | 0 |
| 2.5 | 1.125 | 0 | −1.231 | 0 | 0.085 | 0 | 0 | 0 | 0.017 | 0 | 0 |

-continued

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 2   | 1.846 | 0 | −0.951 | 0 | 0.068 | 0 | 0 | 0 | 0.017 | 0 | 0 |
| 1.5 | 0.593 | 0 | −0.693 | 0 | 0.062 | 0 | 0 | 0 | 0.017 | 0 | 0 |
| 1   | 0.358 | 0 | −0.424 | 0 | 0.076 | 0 | 0 | 0 | 0.017 | 0 | 0 |

These values are particularly well suited for a pupil diameter of 8 mm.

In a second structural shape of the second embodiment, each one of the functions $\beta_i(h)$ satisfies the equation:

$$\beta_i(h) = \frac{h^2}{2}\alpha_{i,j}$$

in which equation j is a whole number which varies as a function of h, in stages, and each $\alpha_{i,j}$, regardless of what i and j are, is a predetermined constant coefficient.

Naturally, each stage corresponds to an annular zone of the correcting portion of the lens.

This structural shape is well adapted to the fact that the diameter of the pupil varies depending on the individuals and the conditions of vision (primarily lighting and proximity).

In a third structural shape of the second embodiment, each one of the functions $\beta_i(h)$ satisfies the equation:

$$\beta_i(h) = \frac{h^2}{2} \sum_{j=0}^{M} \alpha_{i,j} h^j$$

in which equation M is a predetermined whole number and each $\alpha_{i,j}$, regardless of what i and j are, is a predetermined constant coefficient.

This structural shape is similar to the preceding one except that, instead of having functions $\beta_i(h)$ which vary as a function of h in stages, they vary progressively and gently.

The invention also relates, according to a second aspect, to a method for the preparation of a contact or intraocular lens as disclosed above, characterized in that it comprises:
a) a step of determination of the optical path that must be introduced by the correcting portion of this lens;
b) a step of selection of the shape of the posterior surface of said correcting portion, from a series of predetermined shapes, in order to procure optimal comfort for the wearer of the lens;
c) a step of determination of the shape of the anterior surface of said correcting portion, from said shape selected for the posterior surface in step b) and from the optical path determined in step a); and
d) a step of manufacturing said lens with the correcting portion presenting the anterior surface and the posterior surface which were so determined.

Such a method for the preparation of the lens is particularly well suited for fabrication by direct machining: the posterior surface of the lens can have a relatively simple shape, and all the complexity can be transferred to the anterior face, in particular so that the correcting portion introduces the required optical path, and, in the case of a contact lens, to equip this lens with angular stabilization means.

The invention also relates, still according to its second aspect, to an alternate method for the preparation of a contact or intraocular lens as presented above, characterized in that it comprises:
a) a step of determination of the optical path that must be introduced by the correcting portion of this lens;
b) a step of selection of the shape of the anterior surface of said correcting portion from a series of predetermined shapes, each being axisymmetric;
c) a step of determination of the shape of the posterior surface of said correcting portion from said shape selected for the anterior surface in step b) and from the optical path determined in step a);
d) a step of manufacturing said lens with said correcting portion presenting said posterior surface and anterior surface which were so determined.

This preparation method is particularly well suited for making lenses by molding.

Indeed, because the angular maintenance means, that is, in the case of a contact lens, the angular stabilization means, are generally located on the anterior surface of the lens, one has, in this embodiment, a situation where the angular maintenance means and the surface procuring the correction of astigmatism are located on the anterior side and the posterior side, respectively.

This allows, for the same cylinder value and the same sphere value, realization of all the axes using the same two half molds, where the different values of astigmatism axes are obtained by turning one half mold with regard to the other.

BRIEF DESCRIPTION OF THE DRAWINGS

The disclosure of the invention is now continued with the description of preferred embodiment examples, given for illustrative purpose and in a nonlimiting manner, with regard to the drawings in the appendix.

FIG. 1 is a cross section of a contact lens according to the invention along its vertical meridian plane;

FIG. 2 is a top view of this lens;

FIG. 3 is a partial top view of this lens showing its center, with enlargement with regard to FIG. 2;

Figure 4:
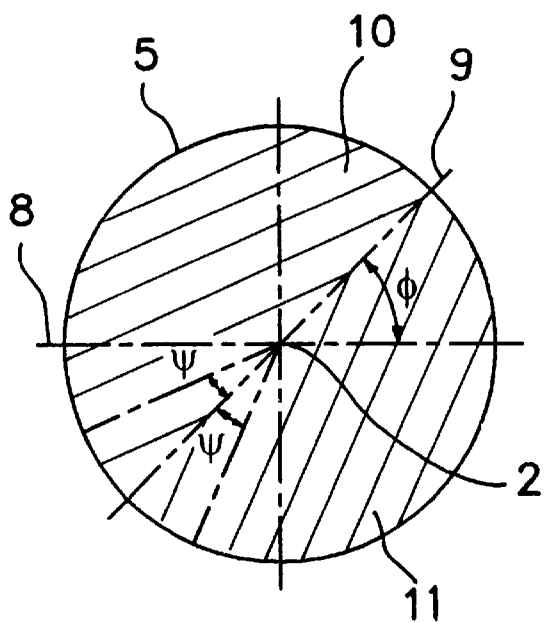
FIG. 4 is a top view of the correcting portion of the lens in a first embodiment example where this portion is divided into two sectors in which the correction axis, of the toric type, is, with regard to the required axis $\phi$, respectively inclined by plus or minus the angle $\psi$.

The contact lens 1 illustrated in the drawings is, in the classic manner, centered about an optical axis 2, and presents a convex anterior face 3 and a concave posterior face 4.

The latter face is spherical, while the anterior face 3 presents a shape which allows, in combination with a posterior face 4, the acquisition of correction of vision required for the wearer, and also the acquisition of stabilization, both with centering and rotation, of this lens with respect to the eye, thanks to the dynamic effect regularly caused by blinking the eyelids.

More specifically, the correction of the vision is obtained by the portion 5 located between the optical axis 2 and the circle located at 4 mm from this axis, shown in broken lines on FIGS. 2 and 3, while the stabilization means consists, in a well known manner, of a progressive thinning or lightening, toward the edge, of the superior portion 6 and the inferior portion 7, respectively, of the lens, along the vertical direction (axis of the blinking of the eyelids), where the portions 6 and 7 cooperate with the upper eyelid and the lower eyelid, respectively, to achieve the effect that the axis 2 coincides with the optical axis of the eye of the wearer and to achieve that the reference meridian plane 8 of the lens 1 coincides with the horizontal meridian plane of the eye of the wearer.

The illustrated lens is designed to effect a correction of an astigmatism with axis $\phi$, that is a correction oriented along a plane 9 (FIG. 3) which presents an angular separation $\phi$ with regard to the reference meridian plane 8.

Let A be any point on the anterior surface 3 of the lens. Its position is defined by the coordinates h and $\theta$, where h is the distance separating the point A from the optical axis 2 of the lens, and $\theta$ is the angular difference between the meridian plane containing the point A and the reference plane 8.

Figure 5:
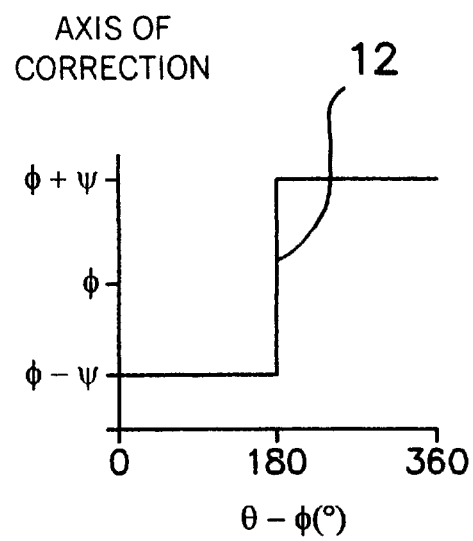
FIG. 5 is a graph showing how the axis of the correction of the toric type varies, where the angle $\theta-\phi$, which is expressed in degrees (°), is plotted on the abscissa, while the axis of correction of the toric type is plotted on the ordinate.
Figure 6:
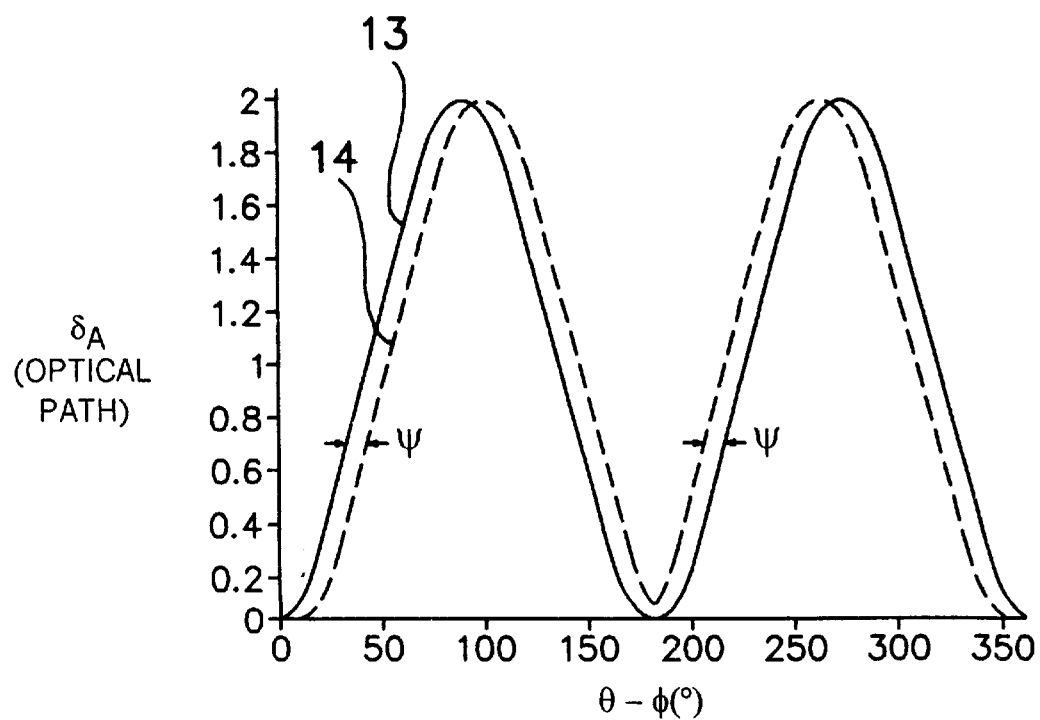
FIG. 6 is a graph showing how the optical path introduced by a conventional correcting portion of the toric type (full line curve) varies, and how the optical path introduced by the correcting portion shown in FIG. 4 (broken line curve) varies, where the angle $\theta-\phi$, which is expressed in degrees (°), is plotted on the abscissa, and the optical path, to the nearest $h^2/2$, is plotted on the ordinate, in the case where the cylinder value required for the correction is 2 diopters.

In the embodiment example shown in FIGS. 4–6, the correcting portion 5 is not oriented in its entirety along plane 9, rather it is divided by this same plane into two sectors 10 and 11, procuring a correction of astigmatism whose axis is inclined in one direction and then in the other by the angle $\psi$ with regard to the axis $\phi$.

More specifically, in sector 10 corresponding to the set of points A for which the angle $\theta-\phi$ is between 0° and 180°, the correction of astigmatism is oriented along the axis $\phi-\psi$, while for sector 11, which corresponds to the set of points A for which the angle $\theta-\phi$ is between 180° and 360°, the correction of astigmatism is inclined along the axis $\phi+\psi$, as shown by the curve 12 of FIG. 5.

As is known, the optical path introduced by a conventional lens for correcting astigmatism satisfies, according to the parabolic approximation, the equation:

$$\delta^{\text{①}}_{ionque}(h, \theta) = \frac{C}{2} h^2 \sin^2(\theta - \phi)$$

Key: 1 Toric in which equation C is the cylinder value required for the correction of the astigmatism.

In the case of a lens having the correcting portion illustrated in FIG. 4, the angle $\phi$ is replaced by the angle $\phi-\psi$ in sector 10 and by the angle $\phi+\psi$ in sector 11. To obtain the best possible results, for sectors 10 and 11, one does not directly apply the cylinder powers C, but a power which approaches C of the value C+c, c being a constant.

Thus, the optical path introduced by the correcting portion 5 illustrated in FIG. 4 satisfies the following equation:

$$\delta_A(h, \theta) = \frac{C+c}{2} h^2 \sin^2(\theta - \phi + \eta)$$

in which equation $\eta$ is equal to $\psi$ for $\theta-\phi$ between 0° and 180° and equal to $-\psi$ for $\theta-\phi$ between 180° and 360°, $\psi$ being a constant.

Curve 13 of FIG. 6, drawn in full lines, shows how the function $2\delta_{toric}/h^2$ varies as a function of $\theta-\phi$ in the case where the cylinder value is 2 diopters, that is, in practice, it illustrates the function $2 \sin^2(\theta-\phi)$, which is, moreover, equal to the function $1-\cos[2(\theta-\phi)]$.

Curve 14, drawn in broken lines, shows the function $2\delta_A(h,\theta)/h^2$, that is:

for $\theta-\phi$ between 0° and 180° (sector 10: (C+c)$\sin^2[\theta-(\phi-\psi)]$; and for $\theta-\phi$ between 180° and 360° (sector 11): (C+c)$\sin^2[\theta-(\phi+\psi)]$, c being zero or negligible.

Curve 14 thus corresponds, for $\theta-\phi$ between 0° and 180° (sector 10), to curve 13 displaced to the right by the value $\psi$, while for $\theta-\phi$ between 180° and 360° (sector 11), curve 14 corresponds to curve 13 shifted to the left by $\psi$.

As indicated, in this example, the cylindrical optical power C is 2 diopters. The values of c and $\psi$, determined by optimization, as explained below, for a pupil diameter of 6 mm, are 0.04 diopter and 9.1°, respectively.

It should be noted that it is possible to express the optical path introduced by the correcting portion 5 illustrated in FIG. 4 in the form of a Fourier series development:

$$\delta_A(h, \theta) = \frac{h^2}{2} \sum_{i \in N} \alpha_i \cos i[(\theta - \phi)]$$

in which equation:

N is the set of whole numbers; and each $_i$, for i$\cup$N, is a constant coefficient.

In order to facilitate the practical fabrication of a lens comprising sectors such as 10 and 11, and in particular to avoid the possible existence of a crest between the sectors, thus avoiding discomfort which this crest could cause for the wearer, it is possible to keep only the first harmonics, for example, up to i=3 or i=10, which correspond to low pass filtering, and possibly to effect an optimization of the remaining coefficients $\alpha_i$ in order to obtain the best results, in the manner which will be explained below.

By so proceeding, for i up to 10, one attains, for example, the following coefficients, still for correction of an eye requiring a cylindrical optical power of 2 diopters, with a pupil diameter of 6 mm:

| $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|
| 1.034 | −0.299 | −0.942 | 0.165 | 0.000 | 0.048 | 0.000 | 0.022 | 0.000 | 0.010 | 0.000 |

Figure 8:
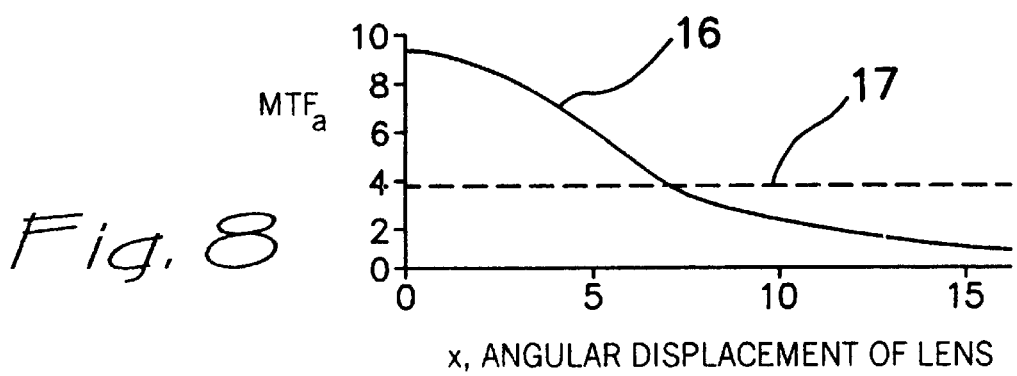
FIG. 8 is a graph illustrating the angular tolerance of a conventional toric lens whose cylinder value is 2 diopters with a pupil diameter of 6 mm, where the angular displacement with regard to the required position, which is expressed in degrees (°), is plotted on the abscissa, while the value of MTFa, calculated for the difference between the optical path introduced by this conventional toric lens when it is angularly displaced, is plotted on the ordinate, and the optical path introduced by the same lens when its angular position is correct (a different curve would be obtained with different values of cylinder or pupil diameter; in general, the angular misalignment tolerance of a conventional lens decreases with increasing cylinder and increasing pupil size)

FIG. 8 is a graph illustrating, by curve 16, the calculated value of MTFa with a pupil diameter of 6 mm, for a difference of the optical path:

$$\delta_{toric}(h, \theta-x) - \delta_{toric}(h, \theta)$$

where $\delta_{toric}(h,\theta)$ is the optical path introduced by a conventional toric lens whose cylinder value is 2 diopters, while x is the angular displacement of the lens with regard to its ideal position, and where this displacement is plotted on the abscissa and the MTFa on the ordinate. It should be noted that a different curve would be obtained with different values of cylinder or pupil diameter; in general, the angular misalignment tolerance of a conventional lens decreases with increasing cylinder and increasing pupil size. In the present application, a "class" of lens generally refers to lenses having the same cylinder and pupil diameter.

Thus, curve 16 represents, for each value of x, the MTFa of an optical system formed by an eye with normal vision having a pupil diameter of 6 mm and an imaginary lens corresponding to the perturbation introduced by the angular displacement of the above-mentioned lens.

One can see that, in the absence of perturbation (displacement of 0°), the value of MTFa is approximately 9.3, and that, starting with this value, MTFa decreases regularly as the angular displacement increases.

If one calculates MTFa for the composed system by the same eye and by a lens presenting a spherical optical power of more or less 0.25 diopter, one obtains a value of MTFa of approximately 3.75.

However, one takes into consideration that the threshold of perception for the wearer of a lens of a degradation of the optical performance generally corresponds to a displacement of 0.25 diopter of spherical optical power.

The MTFa value of 3.75 thus corresponds, in the present example, to the threshold below which the wearer of the lens starts to perceive a degradation.

The horizontal line 17, traced in broken lines in FIG. 8, illustrates this threshold of perception.

One sees that the intersection of curves 16 and 17 is located roughly for an angular displacement of 7°.

This means that a wearer equipped with a conventional lens for correction of astigmatism, under the conditions of the present example (pupil diameter of 6 mm and cylinder value of 2 diopters), starts to perceive a degradation of the performance of the lens if it is angularly displaced more than by plus or minus 7° with regard to the ideal orientation.

Figure 7:
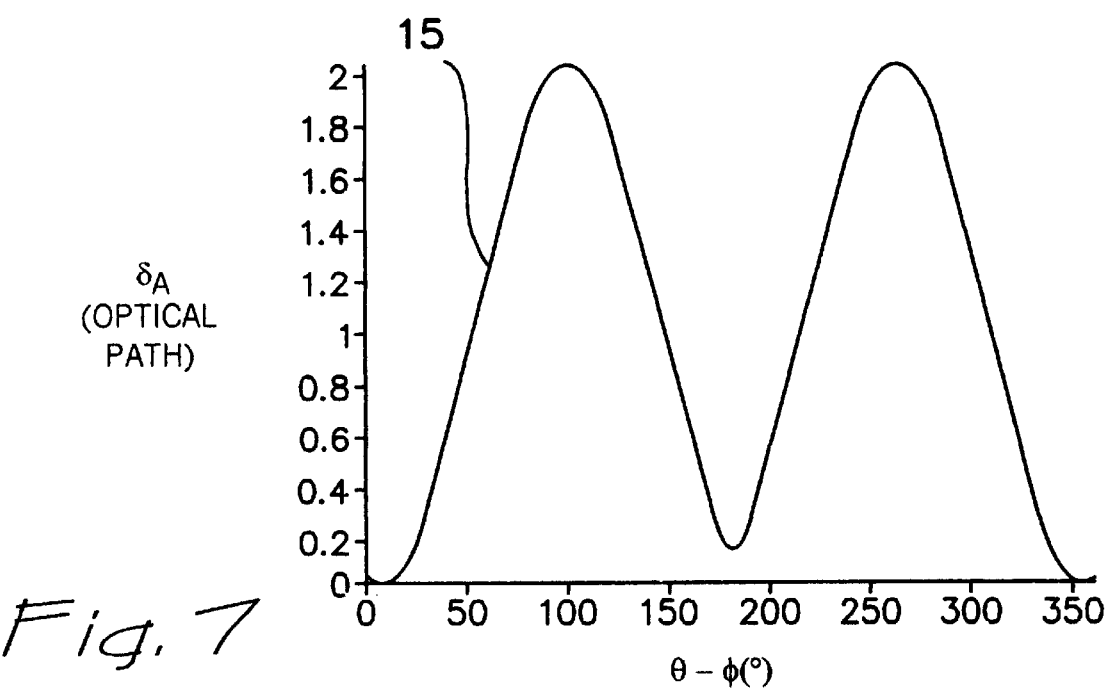
FIG. 7 is a graph similar to that of FIG. 6, showing the optical path obtained by performing low pass filtering and an optimization of the optical path shown in full lines on FIG. 6.
Figure 9:
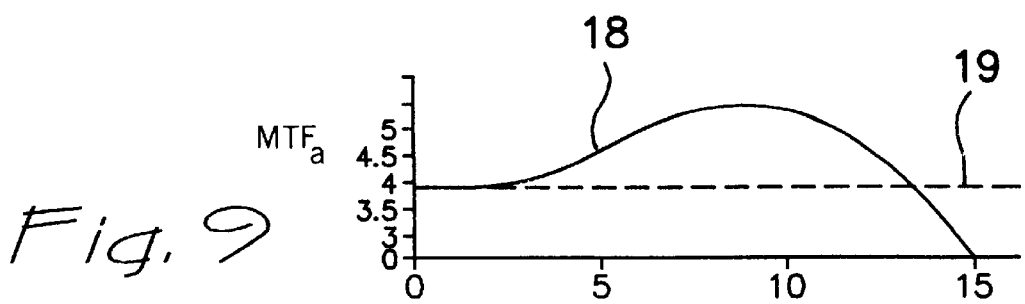
FIG. 9 is a graph similar to that of FIG. 8, except that it represents the value of MTFa calculated for the difference between the optical path introduced by the lens whose optical path is illustrated in FIG. 7 and the optical path introduced by the above-mentioned conventional toric lens (cylinder value of 2 diopters), when its angular position is correct.

FIG. 9, in a similar manner to FIG. 8, illustrates the MTFa calculated under the same conditions (i.e., with a lens in the same class), but where $\delta_{toric}(h,\theta-x)$ is replaced by $\delta_A(h,\theta-x)$, with $\delta_A(h,\theta-x)$, which is the optical path shown in FIG. 7: curve 18, drawn in full lines, illustrates this MTFa, and line 19 drawn in broken lines, the same threshold as in FIG. 8.

Curve 18 represents, for each value of x, the MTFa of an optical system formed by an eye with normal vision and a pupil diameter of 6 mm and of an imaginary lens corresponding to the perturbation introduced at one and the same time from the fact of the replacement of the conventional lens by the lens having the optical path shown in FIG. 7 and from the fact of the angular displacement of this latter lens.

One sees that, in the absence of displacement (x=0), MTFa takes on the exact threshold value illustrated by line 19, and this up to a displacement of approximately plus or minus 2°, above which the value of MTFa increases to attain a maximum for a displacement value slightly larger than 9°, corresponding. essentially to the angle ψ, the value of MTFa then decreases regularly and intersects line 19 for a displacement of approximately 13°.

While the conventional lens, whose optical path is represented by curve 13, presents an angular tolerance $\Delta\phi$ of 14°, the range of variation being [−7°,7°], the lens according to the invention, whose optical path is illustrated by curve 15, presents an angular tolerance of 26°, that is a range of variation of [−13°,13°], or a gain in amplitude of the range of variations of 90%.

As indicated above, the above-mentioned coefficients $\alpha_i$, for i up to 10, presenting such a result, were determined by optimization. This consisted in seeking to obtain a maximum for $\Delta\phi'$.

More specifically, starting with certain coefficients $\alpha_i$, for i up to 10, determined previously as explained below, a classic optimization method was used, such as the simplex, consisting of first individually varying each coefficient by a certain quantity in order to determine the partial derivative of the overall function at the starting point for each of the coefficients, and thus the direction of variation of the nappe, then one can alternately vary the coefficients until a maximum is obtained for $\Delta\phi'$.

The starting coefficients $\alpha_i$, for i up to 10, were simply determined by a Fourier series decomposition of the optical path corresponding to curve 14.

The latter curve itself had to be previously optimized by seeking, in a similar manner, the best performing values for c and for ψ.

More generally, for correcting an astigmatism with a cylinder value of C, one can determine the angular tolerance $\Delta\phi$ of a conventional toric lens, introducing the optical path $\delta_{toric}(h,\theta)$, and the angular tolerance $\Delta\phi'$ of a lens which conforms to the invention, introducing the optical path $\delta_A(h,\theta)$, in the following manner:

$\Delta\phi$ is the amplitude of the range of variation [−½Δφ, ½Δφ'] of a variable x, which amplitude is such that for any value x taken in this interval, the following condition is verified:

$$MTFa[\delta_{torique}(h, \theta - x) - \delta_{torique}(h, \theta)] \geq MTFa\left[0, 25\frac{h^2}{2}\right]$$

Key: 1 Toric $\Delta\phi'$ is the amplitude of the range of variation [−½Δφ', ½Δφ'] of a variable x, where the amplitude is such that for any value x taken in this interval, the following condition is verified:

$$MTFa[\delta_A(h, \theta - x) - \delta_{torique}(h, \theta)] \geq MTFa\left[0, 25\frac{h^2}{2}\right]$$

Key 1 Toric

By proceeding with an optimization of $\Delta\phi'$ when the correcting portion 5 of the lens is arranged as shown in FIG. 4, one obtains, depending on the cylinder value, the following results for a pupil diameter of 6 mm:

| (D) | Δφ(°) | Δφ'(°) | C + c(D) | ψ(°) |
|---|---|---|---|---|
| 3 | 9.4 | 17.7 | 3.00 | 6.3 |
| 2.5 | 11.3 | 21.2 | 2.48 | 7.6 |
| 2 | 14.0 | 26.0 | 2.04 | 9.1 |
| 1.5 | 18.8 | 35.6 | 1.49 | 12.7 |
| 1 | 28.2 | 54.0 | 1.00 | 19.1 |

Similarly, for a pupil diameter of 8 mm, one obtains the following values:

| C(D) | Δφ(°) | Δφ'(°) | C + c(D) | ψ(°) |
|---|---|---|---|---|
| 3 | 7.2 | 13.4 | 2.99 | 4.7 |
| 2.5 | 8.5 | 16.2 | 2.50 | 5.7 |
| 2 | 10.6 | 20.2 | 1.98 | 7.2 |
| 1.5 | 14.0 | 27.0 | 1.49 | 9.5 |
| 1 | 21.1 | 40.7 | 0.99 | 14.4 |

One can see that, in all cases, one obtains a very consistent increase in the angular tolerance.

One observes, in general:
on the one hand, that c takes on relatively low values and in all cases. proportionally very small in view of C; and
that the product of the pupil diameter, expressed in millimeters, of C, expressed in diopters, and of ψ, expressed in degrees, remains very close to 114.

Thus, in practice, one can directly take C as cylinder value for each of the sectors 10 and 11 (that is one can consider c to be zero) and choose the angle ψ which following equation:

$$\psi = \frac{114}{C.DP}$$

The angle ψ being expressed in degrees, the cylinder value C in diopters, and the pupil diameter DP in millimeters.

In the case of lenses having a correcting portion of the same type as portion 5 illustrated in FIG. 4, except that low pass filtering as well as an optimization have been applied so that the optical path varies similarly to curve 15, the coefficients $\alpha_i$ having been kept for i up to 10, one obtains the following numbers for a pupil diameter of 6 mm:

| $C_{(D)}$ | $\Delta\phi(°)$ | $\Delta\phi'(°)$ |
|---|---|---|
| 3 | 9.4 | 17.5 |
| 2.5 | 11.3 | 21.0 |
| 2 | 14.0 | 26.6 |
| 1.5 | 18.8 | 35.5 |
| 1 | 28.2 | 54.2 |

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3 | 1.521 | −0.289 | −1.450 | 0.168 | 0 | 0.040 | 0 | 0.019 | 0 | 0.011 | 0 |
| 2.5 | 1.277 | −0.284 | −1.200 | 0.168 | 0 | 0.041 | 0 | 0.019 | 0 | 0.011 | 0 |
| 2 | 1.034 | −0.299 | −0.942 | 0.165 | 0 | 0.048 | 0 | 0.022 | 0 | 0.010 | 0 |
| 1.5 | 0.775 | −0.273 | −0.661 | 0.163 | 0 | 0.040 | 0 | 0.018 | 0 | 0.011 | 0 |
| 1 | 0.522 | −0.261 | −0.383 | 0.157 | 0 | 0.038 | 0 | 0.018 | 0 | 0.010 | 0 |

Similarly, for a pupil diameter of 8 mm, one obtains the following numbers:

| $C_{(D)}$ | $\Delta\phi(°)$ | $\Delta\phi'(°)$ |
|---|---|---|
| 3 | 1.2 | 13.3 |
| 2.5 | 8.5 | 16 |
| 2 | 10.6 | 20.1 |
| 1.5 | 14.0 | 26.9 |
| 1 | 21.1 | 40.8 |

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3 | 1.502 | −0.216 | −1.465 | 0.121 | 0 | 0.031 | 0 | 0.014 | 0 | 0.008 | 0 |
| 2.5 | 1.261 | −1.218 | −1.215 | 0.126 | 0 | 0.030 | 0 | 0.014 | 0 | 0.008 | 0 |
| 2 | 1.015 | −0.214 | −0.964 | 0.127 | 0 | 0.031 | 0 | 0.014 | 0 | 0.008 | 0 |
| 1.5 | 0.766 | −0.212 | −0.695 | 0.124 | 0 | 0.030 | 0 | 0.014 | 0 | 0.008 | 0 |
| 1 | 0.516 | −0.203 | −0.425 | 0.121 | 0 | 0.030 | 0 | 0.014 | 0 | 0.008 | 0 |

One observes that a gain between $\Delta\phi'$ and $\Delta\phi$ varies between 86 and 92%.

Moreover, concerning coefficients $\alpha_i$, one observes that the sum of their squares, if one excludes $\alpha_0$ and $\alpha_2$, varies between 0.095 and 0.119. This demonstrates the introduced optical power is not purely spherocylindrical, because if that had been the case, the sum in question would have been zero.

It is recalled, in this regard, that if the correction provided had been purely spherocylindrical, all the coefficients other than $\alpha_0$ and $\alpha_2$ would have been zero; the efficient $\alpha_0$ being equal to C/2 and the coefficient $\alpha_2$ being equal to −C/2.

Figure 10:
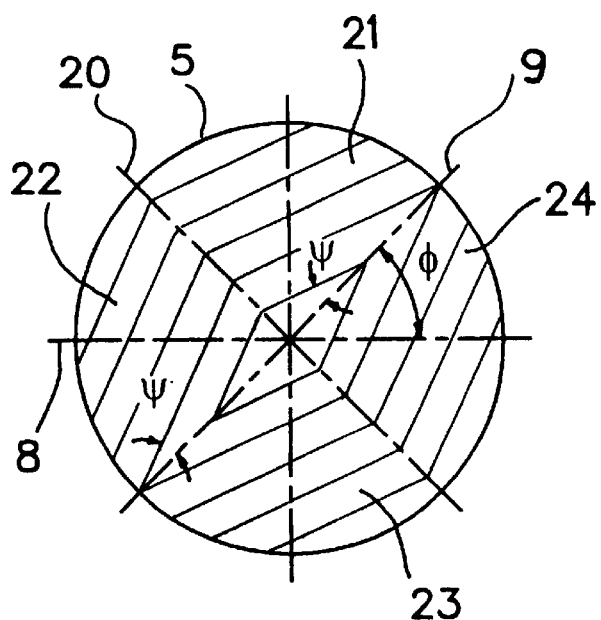
FIGS. 10–13 are similar to FIGS. 4–7, respectively, but for a second embodiment example of the invention in which the correcting portion is divided into four sectors, whose axis is alternately inclined by plus or minus the angle $\psi$.
Figure 11:
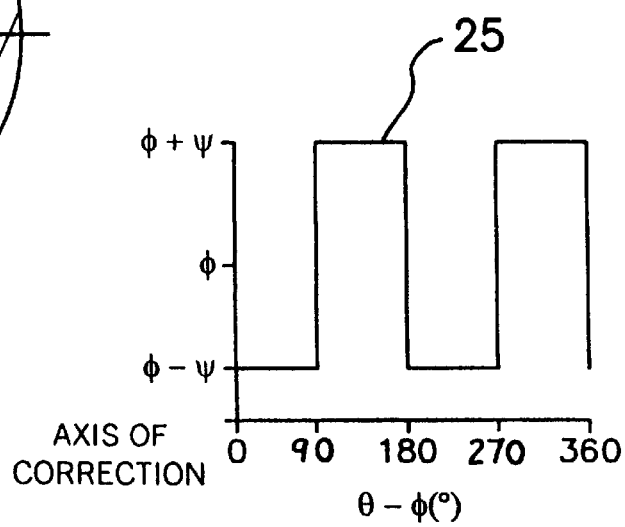
Figure 12:
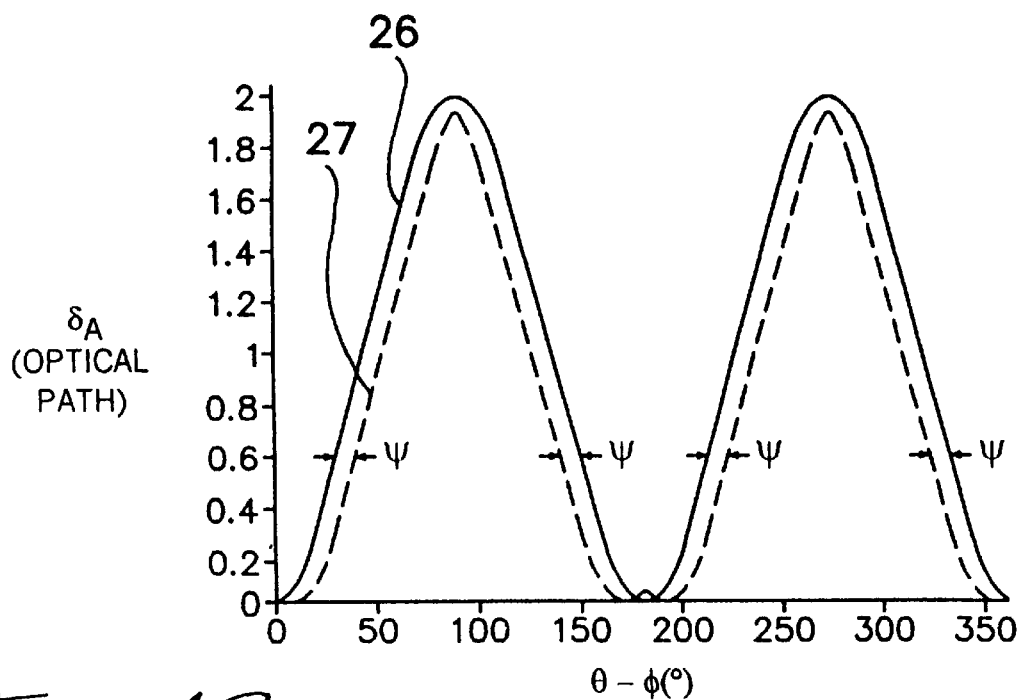

In the embodiment example shown in FIGS. 10–12, the correcting portion 5 is not divide into two sectors by the plane 9, but into four sectors respectively by plane 9 and by plane 20 orthogonal to plane 9, the sectors 21–24 so delimited providing a correction of the astigmatism whose axis is alternately inclined in one direction and in the other direction by the angle ψ with regard to the axis φ. More specifically, in the opposite sectors 21 and 23 corresponding to the set of the points A for which the angle θ−φ is between 0° and 90° and between 180° and 270°, the correction of the astigmatism is oriented along the axis φ−ψ, while for the opposite sectors 22 and 24, which correspond to the set of the points A for which the angle θ−φ is between 90° and 180° and between 270° and 360°, the correction of the astigmatism is oriented along the axis φ+ψ, as shown by curve 25 of FIG. 11.

Taking again the same notations as for the lens whose correcting portion 5 is illustrated in FIG. 4, the optical path introduced by the correcting portion 5 illustrated in FIG. 10 satisfies the following equation:

$$\delta_A(h, \theta) = \frac{C+c}{2} h^2 \sin^2(\theta - \phi + \eta)$$

in which equation η is equal to ψ for θ−φ between 0° and 90° and for θ−φ between 180° and 270°, and equal to −ψ for θ−φ between 90° and 180° and for θ−φ between 270° and 360°, c and ψ being constants.

Curve 26 of FIG. 12, drawn in full lines, is exactly identical to curve 13 of FIG. 6, that is it shows how the function $$2\delta_{toric}/h^2$$

varies as a function of θ−φ in the case where the cylinder value is 2 diopters.

Curve 27, which is drawn in full lines, shows the function $$2\delta_A(h,\theta)/h^2$$

that is:

for θ−φ between 0° and 90° (sector 21) and for θ−φ between 180° and 270° (sector 23): $(C+c)\sin^2[\theta-(\phi-\psi)]$;

for θ−φ between 90° and 180° (sector 22) and for θ−φ between 270° and 360° (sector 24): $(C+c)\sin^2[\theta-(\phi+\psi)]$, c being zero or negligible.

Thus, curve 27 corresponds, for θ−φ between 0° and 900 (sector 21) and for θ −φ between 180° and 270° (sector 23), to curve 26 displaced by the value ψ to the right, while for the other values of θ−φ (sectors 22 and 24), curve 27 corresponds to curve 13 displaced by ψ to the left.

More specifically, in the illustrated example, the cylindrical optical power C is 2 diopters, while the values of c and of ψ, determined by optimization as explained above for a pupil diameter of 6 mm, are 0.00 diopter and 7.4 degrees, respectively.

Figure 13:
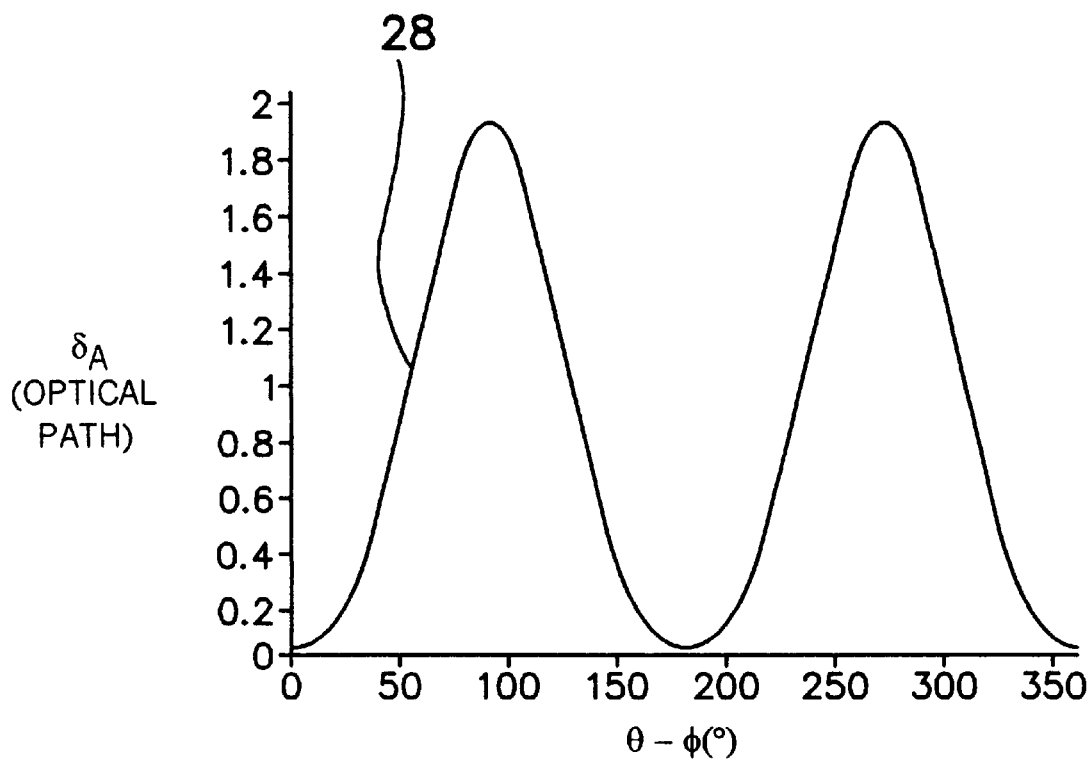

The optical path illustrated by curve 28 of FIG. 13 had been obtained by proceeding, with respect to the optical path represented by curve 27, in the same manner as the optical path illustrated by curve 15 had been obtained arising from the optical path illustrated by curve 14, the coefficient $\alpha_i$ being the following:

| $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|
| 0.830 | 0 | −0.940 | 0 | 0.112 | 0 | 0 | 0 | 0.023 | 0 | 0 |

In general, one can see that curve 28 is entirely similar to curve 27, except for, on the one hand, the fact that it does not present, in the vicinity of θ−φ equal to 0° and θ−φ equal to 180°, a W shape, but a simple U shape, corresponding to that of a smoothed W, and, on the other hand, the maximum reached for θ−φ equal to 90° and for θ−φ equal to 270°, respectively, is less important than the maximum of curve 27.

One observes that the curves 14 and 15 have a periodicity of 2π, while the curves 27 and 28 have a periodicity of π.

By proceeding to the optimizations as indicated above, one obtains, for the lens whose correcting portion 5 corresponds to that illustrated in FIG. 10, the following values, for a pupil diameter of 6 mm:

| C(D) | Δφ(°) | Δφ'(°) | C + c(D) | ψ(°) |
|---|---|---|---|---|
| 3 | 9.4 | 13.9 | 2.98 | 5.0 |
| 2.5 | 11.3 | 16.7 | 2.47 | 6.1 |
| 2 | 14.0 | 21.0 | 2.00 | 7.4 |
| 1.5 | 18.8 | 28.4 | 1.47 | 10.5 |
| 1 | 28.2 | 44.2 | 0.95 | 16.7 |

Similarly, for a pupil diameter of 8 mm, one obtains the following values:

| C(D) | Δφ(°) | Δφ'(°) | C + c(D) | ψ(°) |
|---|---|---|---|---|
| 3 | 7.2 | 10.4 | 3.00 | 3.6 |
| 2.5 | 8.5 | 12.6 | 2.48 | 4.5 |
| 2 | 10.6 | 15.9 | 1.98 | 5.7 |
| 1.5 | 14.0 | 21.3 | 1.49 | 7.5 |
| 1 | 21.1 | 32.7 | 0.97 | 12.0 |

One observes that the increase in the range of tolerance varies between 46 and 55% and that, as in the preceding embodiment example, the value of c remains low.

The contact lens having an optical path of the type illustrated by curve 28, that is an optical path which has been subjected to low pass filtering and optimization of the coefficients, gives the following numbers for a pupil diameter of 6 mm:

| $C_{(D)}$ | Δφ(°) | Δφ'(°) |
|---|---|---|
| 3 | 9.4 | 13.1 |
| 2.5 | 11.3 | 16.5 |
| 2 | 14.0 | 20.8 |
| 1.5 | 18.8 | 28.2 |
| 1 | 28.2 | 43.8 |

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3 | 1.331 | 0 | −1.472 | 0 | 0.114 | 0 | 0 | 0 | 0.023 | 0 | 0 |
| 2.5 | 1.071 | 0 | −1.206 | 0 | 0.107 | 0 | 0 | 0 | 0.024 | 0 | 0 |
| 2 | 1.830 | 0 | −0.940 | 0 | 0.112 | 0 | 0 | 0 | 0.023 | 0 | 0 |
| 1.5 | 0.575 | 0 | −0.667 | 0 | 0.108 | 0 | 0 | 0 | 0.024 | 0 | 0 |
| 1 | 0.332 | 0 | −0.384 | 0 | 0.105 | 0 | 0 | 0 | 0.025 | 0 | 0 |

Similarly, for a pupil diameter of 8 mm, one obtains the following numbers:

| $C_{(D)}$ | Δφ(°) | Δφ'(°) |
|---|---|---|
| 3 | 7.2 | 10.4 |
| 2.5 | 8.5 | 12.4 |
| 2 | 10.6 | 15.1 |
| 1.5 | 14.0 | 21.1 |
| 1 | 21.0 | 32.5 |

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3 | 1.365 | 0 | −1.471 | 0 | 0.081 | 0 | 0 | 0 | 0.016 | 0 | 0 |
| 2.5 | 1.125 | 0 | −1.231 | 0 | 0.085 | 0 | 0 | 0 | 0.017 | 0 | 0 |
| 2 | 1.846 | 0 | −0.951 | 0 | 0.068 | 0 | 0 | 0 | 0.017 | 0 | 0 |
| 1.5 | 0.593 | 0 | −0.693 | 0 | 0.062 | 0 | 0 | 0 | 0.017 | 0 | 0 |
| 1 | 0.358 | 0 | −0.424 | 0 | 0.076 | 0 | 0 | 0 | 0.017 | 0 | 0 |

One can see that the sum of the squares of the coefficients $\alpha_i$, with the exception of i=0 and i=2, is 0.007 each time.

The improvement in the tolerance with respect to an angular displacement is between 41 and 53%.

The lens according to the second embodiment example thus procures a less important broadening of the tolerance to angular displacements. However, one notes that the arrangement of this embodiment example, taking into account the arrangement in opposition of the sectors whose correction axis has the same inclination, presents excellent tolerance of a defect in centering, that is to a defect of coincidence between the optical axis 2 of the lens and the optical axis of the eye.

As for the correcting portion 5 illustrated in FIG. 4, one observes here, in general:

on the one hand, that c takes on relatively low values, which in any case are proportionally very small in view of C; and that the product of the pupil diameter, expressed in millimeters, of C, expressed in diopters, and of $\psi$, expressed in degrees, remains very close to 90.

In practice, one can thus directly take C as a cylinder value for each of sectors 21–24 (that is that c equals zero) and choose the angle $\psi$ which satisfies the following equation:

$$\psi = \frac{90}{C.DP}$$

The angle $\psi$ being expressed in degrees, the cylinder value C in diopters, and the pupil diameter DP in millimeters.

In the correcting portions 5 illustrated in FIGS. 4 and 10, respectively, the angle $\psi$ is positive, but there is no objection to it being negative.

In the variants of the correcting portion 5 which are not illustrated, the number of sectors is different from two or four, and/or in each of the sectors, the axis and/or cylinder value is(are) different.

One notes, with regard to the coefficients a, in addition to what was stated above for the coefficients $\alpha_0$ and $\alpha_2$, which represent a continuous component and a component of periods, respectively:

that, in all cases, the coefficients $\alpha_i$ rapidly become very small when i increases;

that, in the case of curve 15 (FIG. 7), all the even coefficients are zero starting from i=4 and the coefficients a9 are all on the order of 0.01; and that, in the case of curve 28 (FIG. 13), if one excludes the coefficients $\alpha_0$ and $\alpha_2$, only the coefficients $\alpha_4$ and $\alpha_8$ are not zero.

In general, the optical path $\delta_A(h,\theta)$ introduced by a lens which conforms to the invention, and in particular the optical path illustrated by curves 14, 15, 27 and 28, can be expressed in the form:

$$\delta_A(h,\theta) = \delta_{toric}(h,\theta) + \delta_{atoric}(h,\theta)$$

$\delta_{atoric}(h,\theta)$ being a function such that, at constant h, it varies as a function of 0 with a period of 2, and differently from $\sin^2(\theta-\phi)$.

In the case of optical paths 14 and 27, $\delta_{atoric}(h,\theta)$, that is the atoric component of the optical path $\delta_A(h,\theta)$, corresponds to the difference between the optical path which is represented by curve 14 and the one represented by curve 13, respectively; and to the difference between the optical path represented by curve 27 and the one represented by curve 26.

Figure 14:
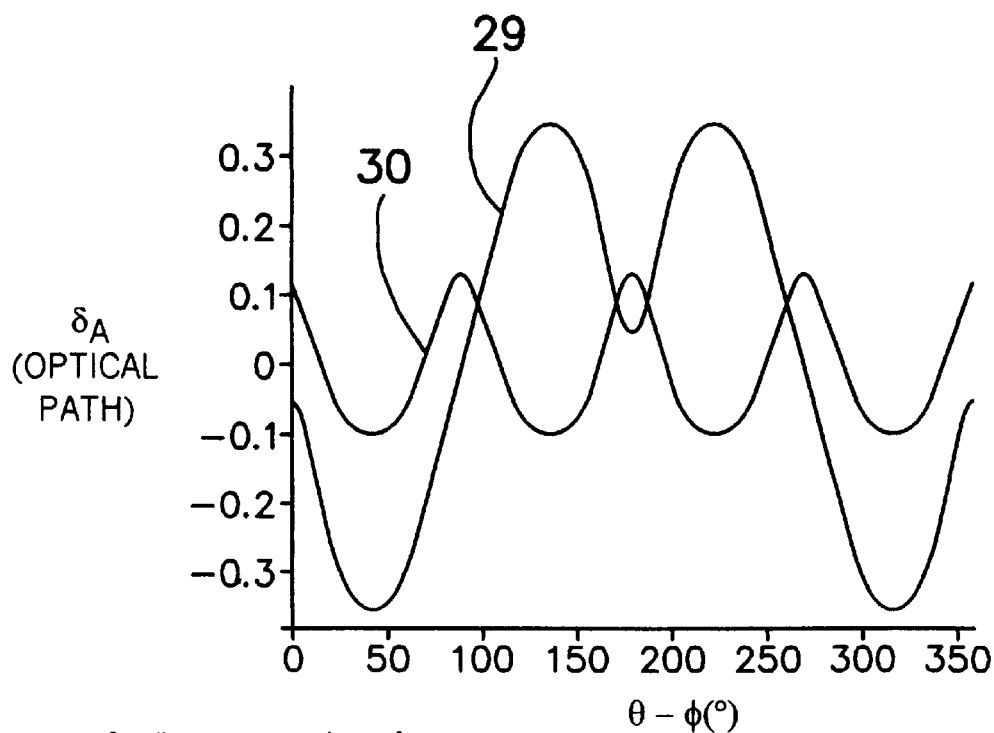
FIG. 14 is a graph similar to that of FIGS. 7 and 13 but showing the atoric component of the optical path illustrated by curve 15 and by curve 28, respectively.

In the case of the optical paths represented by curves 15 and 28, respectively, $\delta_{atoric}(h,\theta)$ is illustrated by curves 29 and 30, respectively, of FIG. 14.

More specifically, each of these curves is given by the above-mentioned coefficients $\alpha_1$ and $\alpha_3$ to $\alpha_{10}$, that is by the set of coefficients $\alpha_i$, with the exception of $\alpha_0$ and $\alpha_2$.

One notes that curve 29 is close to the difference between curve 13 and curve 15, without, however, being equal to this difference because the toric component $\delta_{toric}(h,\theta)$ of the optical path represented by curve 15 is not exactly equal to the optical path represented by curve 13 since $\alpha_0=1.034$ (and not C/2 or 2/2=1.000 diopter) and since $\alpha_2=-0.942$ (and not $-C/2$, or $-1.000$).

The same observation applies to curve 30, which does not correspond to the difference between curve 26 and curve 28, since $\alpha_0=0.830$ and $\alpha_2=-0.940$.

π

One notes that curve 29 has a period of $2\pi$ and that the portions of curve 29 located between 0 and $\pi$ (180°) and between $\pi$ and $2\pi$ (360°), respectively, are symmetrical, that is one is the mirror image of the other.

Curve 29 decreases to approximately $\theta-\phi=45°$; it increases to approximately $\theta-\phi=135°$; decreases up to $\theta-\phi=180°$; increases up to $\theta-\phi=$approximately 225°; decreases up to approximately $\theta-\phi=315°$; then increases up to $\theta-\phi=360°$.

Curve 30 has a period of $\pi/2$. It decreases from $\theta-\phi=0°$ to $\theta-\phi=45°$, then increases up to $\theta-\phi=90°$.

For a pupil diameter of 8 mm, one obtains curves which vary in a similar manner to curves 29 and 30, respectively, but with a smaller amplitude of variation.

With regard to the numerical values which have been given until now, one notes:

for the correcting portions 5 of the type illustrated in FIGS. 4 and 10, that one still obtains good results until one deviates by ±0.125 diopter for the value of C+c and by ±1° for the value of $\psi$;

that, for the correcting portions introducing an optical path of the type shown in FIGS. 7 and 13, one can deviate from the coefficients $\alpha_i$ given above as long as the distance, in the mathematical sense of the term, remains less than 0.05, that is as long as:

$$\sqrt{\sum_{i \in E}(\alpha_i - \alpha_i')^2} \le 0.05$$

the coefficients $\alpha_i$ of this formula being the coefficient that exist in practice (with the tolerance) and the coefficients $\alpha_i'$ being the nominal coefficients, that is those given by the tables represented in the preceding description made in support of the drawings.

In the embodiment examples that have not been illustrated, the optical path also varies as a function of h.

In the first example of this type, the optical path introduced by the correcting portion of the lens is written in the form:

$$\delta_A(h,\theta) = \sum_{i \in E} \beta_i(h)\cos[i(\theta-\phi)]$$

in which equation:

E is a finite set comprising the whole numbers starting from 0; and $\beta_i(h)$ is a set of functions satisfying the equation:

$$\beta_i(h) = \frac{h^2}{2}\alpha_{i,j}$$

j being a whole number which varies as a function of h, by stages, each $\alpha_{ij}$, regardless of what i and j are, being a predetermined constant coefficient.

The cylindrical optical power, at constant θ, thus remains constant, as a function of h, in zones corresponding to each of the stages.

In another example of the above-mentioned type, $\beta_i(h)$ is a set of functions satisfying the equation:

$$\beta_i(h) = \frac{h^2}{2}\sum_{j=0}^{M}\alpha_{i,j}h^j$$

in which equation M is a predetermined whole number and each $\alpha_{i,j}$, regardless of what i and j are, is a predetermined constant coefficient.

The cylindrical optical power, at constant θ, thus varies gently as a function of h according to a polynomial function.

Because the shape of the posterior surface 4 is known (spherical in the present example), and because the index of refraction of the material of the lens is known, and if one fixes the thickness of the latter at the center, it is possible to determine, in a well known manner, the coordinates of the different points A of the anterior surface 3 from the optical path δ(h,θ), which here is chosen, at least for h located between 0.4 mm and 2.4 mm, such that is satisfies the equation:

$$\delta(h,\theta)=\delta_o+\delta_A(h,\theta)$$

in which equation $\delta_0$ is an arbitrary constant and $\delta_A(h,\theta)$ is taken with the above-mentioned tolerances.

The optical path so defined allows the determination of a shape which is suitable for the anterior surface of the correcting portion 5.

In a variant of the lens 1, the posterior face 4, instead of being purely spherical, presents an aspherical shape, which is mechanically adapted to the geometry of the cornea of the eye intended to receive this lens, this posterior surface being in practice chosen from a series of predetermined shapes based on tests carried out on the eye to be equipped.

In one other variant of the lens 1, one chooses the shape of the anterior surface 3 among a series of known surfaces, and it is a suitable shape for the posterior surface 4 which one determines.

In other variants which have not been represented, the lightenings 6 and 7 are replaced by different means for stabilization of centering and rotation, and notably by dynamic bosses, such as those described in French Patent No. 2 760 853 or by a ballast prism located in the low part, possibly completed by a lightening in the top part.

In other embodiments, the lens according to the invention is provided so as to effect not only a correction of astigmatism, but also a correction of myopia or hyperopia and/or progressive simultaneous vision correction of presbyopia.

The optical path δ(h,θ) mentioned above is then completed to satisfy the inequation:

$$\delta_{inf}(h,\theta)\leq\delta(h,\theta)\leq\delta_{sup}(h,\theta)$$

where $\delta_{inf}(h,\theta)$ and $\delta_{sup}(h,\theta)$ satisfy, respectively, the following equations:

$$\delta_{inf}(h,\theta)=\delta_0+\delta_S(h)+\delta_p(h)+\delta_A(h,\theta)-0.09h^2$$

$$\delta_{sup}(h,\theta)=\delta_{inf}(h,\theta)+0.18h^2$$

in which equations, h and all the δ are expressed in meters (m):

$\delta_s(h)$ is, in the case of spherical correction, the optical path provided for this correction, satisfying the equation:

$$\delta_s(h) = \frac{P_{VL}}{2}h^2$$

in which equation $P_{VL}$ is the spherical power required to correct the myopia or hyperopia of said eye, expressed in diopters (D);

$\delta_p(h)$ is, in the case of progressive simultaneous vision correction, the optical path provided for this correction, satisfying the equation:

$$\delta_p(h) = \sum_{k=0}^{k=9}\frac{\gamma_{2k}}{2k+2}10^{6k}h^{2k+2}$$

the series of coefficients $\gamma_{2k}$ being defined by the respective one of the nine lists SA, SB, SC, MA, MB, MC, LA, LB, LC of coefficients given below:

| k | SA | SB | SC |
|---|---|---|---|
| 0 | 1.398800E+00 | 3.093330E+00 | 4.605640E+00 |
| 1 | −2.160020E+00 | −4.751140E+00 | −5.235240E+00 |
| 2 | 1.337720E+00 | 2.913640E+00 | 2.458240E+00 |
| 3 | −4.327890E−01 | −9.378340E−01 | −6.301520E−01 |
| 4 | 8.154230E−02 | 1.764900E−01 | 9.787570E−02 |
| 5 | −9.410290E−03 | −2.038990E−02 | −9.616130E−03 |
| 6 | 6.736380E−04 | 1.462890E−03 | 6.012020E−04 |
| 7 | −2.914960E−05 | −6.347570E−05 | −2.318560E−05 |
| 8 | 6.978470E−07 | 1.520000E−06 | 5.030000E−07 |
| 9 | −7.091930E−09 | −1.550000E−08 | −4.690000E−09 |

| k | MA | MB | MC |
|---|---|---|---|
| 0 | 1.799020E + 00 | 3.048790E + 00 | 4.144890E + 00 |
| 1 | −1.823880E + 00 | −3.424400E + 00 | −4.233760E + 00 |
| 2 | 8.133470E − 01 | 1.714210E + 00 | 1.949870E + 00 |
| 3 | −2.057150E − 01 | −4.850380E − 01 | −5.212190E − 01 |
| 4 | 3.222470E − 02 | 8.400400E − 02 | 8.739800E − 02 |
| 5 | −3.231690E − 03 | −9.184070E − 03 | −9.410210E − 03 |
| 6 | 2.075120E − 04 | 6.343800E − 04 | 6.468110E − 04 |
| 7 | −8.241900E − 06 | −2.679260E − 05 | −2.734250E − 05 |
| 8 | 1.842050E − 07 | 6.310000E − 07 | 6.460000E − 07 |
| 9 | −1.770040E − 09 | −6.330000E − 09 | −6.520000E − 09 |

| k | LA | LB | LC |
|---|---|---|---|
| 0 | 1.258120E + 00 | 2.3409009E + 00 | 2.660000E + 00 |
| 1 | 2.766510E − 01 | −1.6016233E + 00 | −3.029760E + 00 |
| 2 | −5.863900E − 01 | 8.5580090E − 01 | 1.837520E + 00 |
| 3 | 2.158210E − 01 | −4.0855924E − 01 | −6.361990E − 01 |
| 4 | −3.890640E − 02 | 1.2233248E − 01 | 1.293960E − 01 |
| 5 | 4.063430E − 03 | −2.1406740E − 02 | −1.595350E − 02 |
| 6 | −2.578890E − 04 | 2.2148862E − 03 | 1.205290E − 03 |
| 7 | 9.821560E − 06 | −1.3380186E − 04 | −5.450000E − 05 |
| 8 | −2.065710E − 07 | 4.3658573E − 06 | 1.350000E − 06 |
| 9 | 1.845210E − 09 | −5.9468409E − 08 | −1.410000E − 08 |

(E and the number which follows represent the exponent of the power of 10).

In a variant of this embodiment, the correction of the presbyopia, rather than being effected as above with a higher power at the center than at the periphery of the correcting portion 5, is carried out with a variation in the opposite direction, that is with a power which is lower at the center than at the periphery of the correcting portion.

In such a case, the optical path introduced by the progressive simultaneous vision correction is not the one given above, rather it is:

$$\delta_p(h) = \frac{P_{ADD}}{2}h^2 - \sum_{k=0}^{k=9} \frac{\gamma_{2k}}{2k+2}10^{6K}h^{2K+2}$$

$P_{ADD}$ being the addition required by the wearer of the lens for near vision, expressed in diopters (D), the series of coefficients $\gamma_{2k}$ being defined by the respective one of the nine lists SA, SB, SC, MA, MB, MC, LA, LB, LC given above.

In the variants which have not been illustrated, the correcting portion such as the portion 5, is evidently not a contact lens but an intraocular lens realized in the form of an implant.

Numerous other variants are possible depending on the circumstances, and in this regard it is recalled that the invention is not limited to the examples which have been described and represented.

What is claimed is:

1. Contact or intraocular lens comprising a correcting portion (5) in order to correct the vision of a possibly myopic or hyperopic and/or possibly presbyopic astigmatic eye, comprising an optical axis (2) and a reference meridian (8); characterized in that it introduces, for correction of only the astigmatism, an optical path varying as a function of the distance (h) with regard to the optical axis (2) and as a function of the angular separation (θ) with regard to the reference meridian (8), at least when this distance is between 0.4 mm and 2.4 mm, according to the following equation:

$$\delta_A(h,\theta) = \delta_{toric}(h,\theta) + \delta_{atoric}(h,\theta)$$

in which equation:

$\delta_{toric}(h,\theta)$ is a cylindrical optical path (13,26) which satisfies, according to the parabolic approximation, the expression $\delta_{toric}(h,\theta) = C/2\, h^2 \sin^2(\theta-\phi)$, where $\phi$ is the axis required in order to correct the astigmatism of said eye expressed in angular separation with regard to said reference meridian, and where C is the cylinder value required in order to correct the astigmatism of said eye; and $\delta_{toric}(h,\theta)$ is an optical path (29,30), such that when h is a constant, it varies as a function of θ with a 2π period, and differently from $\sin^2(\theta-\phi)$, this optical path in addition satisfies the condition:

$$\Delta\phi' \geq 1.3\,\Delta\phi$$

in which inequation:

Δφ is the amplitude of the range of variation $[-\tfrac{1}{2}\Delta\phi, \tfrac{1}{2}\Delta\phi]$ of a variable x, amplitude such that for any value of x taken in this interval, the following condition is verified:

$$MTFa[\delta_{toric}(h, \theta - x) - \delta_{toric}(h, \theta)] \geq MTFa\frac{[0.25\,h^2]}{2}$$

Δφ' is the amplitude of the range of variation $[-\tfrac{1}{2}\Delta\phi', \tfrac{1}{2}\Delta\phi']$ of a variable x, amplitude such that for any value of x taken in this interval, the following condition is verified:

$$MTFa[\delta_A(h, \theta - x) - \delta_{toric}(h, \theta)] \geq MTFa\frac{[0.25\,h^2]}{2}$$

the notation $MTFa[f(h,\theta)]$ designating, for an optical path $f(h,\theta)$, the criterion of optic quality calculated from the modulation transfer function produced by this optical path for a predetermined pupil diameter between 4 and 7 mm according to the formula:

$$MTFa[f(h, \theta)] = \int_{v=5}^{v=15}\int_{x=0}^{x=360}\frac{MTF}{360}[f(h,\theta)](v,\chi)\partial v\partial\chi$$

in which formula ν and χ are the polar coordinates in the plane of the angular spatial frequencies, being expressed in cycles per degree and χ in degrees; and in which $MTF[f(h,\theta)](\nu,\chi)$ is the modulation transfer function of the optical path $f(h,\theta)$ according to said polar coordinates.

2. Lens according to claim 1, characterized in that the term $\delta_A(h,\theta)$ satisfies the equation:

$$\delta_A(h,\theta) = \sum_{i\in E}\beta_i(h)\cos[i(\theta-\phi)]$$

in which equation:

N is the set of whole numbers; and $\beta_i(h)$ is a set of functions satisfying the following condition:

$$\sum_{i\in N'}\left[\left(\frac{1}{h_{max}-h_{min}}\int_{h_{min}}^{h_{max}}\frac{2\beta_i(h)}{h^2}dh\right)^2\right] \geq 0.005\ m^{-2}$$

in which inequation N' is equal to N disqualifying 0 and 2, while $h_{min}$ and $h_{max}$ are the minimum distance and the maximum distance, respectively, with regard to the optical axis (2) of the zone of the correcting portion (5) provided to correct the astigmatism.

3. Lens according to claim 2, characterized in that each one of the functions $\beta_i(h)$ satisfies the equation:

$$\beta_i(h) = \frac{h^2}{2}\alpha_i$$

in which equation $\alpha_i$, for i ∈ N, is a constant coefficient.

4. Lens according to claim 3, characterized in that the optical path $\delta_A(h,\theta)$ satisfies the equation:

$$\delta_A(h,\theta) = \frac{C+c}{2}h^2\sin^2(\theta-\phi+\eta)$$

in which equation is equal to ψ for θ−φ between 0° and 180°, and equal to −ψ for θ−φ between 180° and 360°, c and ψ being predetermined constants.

5. Lens according to claim 4, characterized in that the constants c and ψ have, depending on the value of C, the values given by the table below, at ±0.125 diopter (D) for C+c, and at ±1° for ψ:

| C (D) | C + c (D) | ψ |
|---|---|---|
| 3 | 3.00 | 6.3° |
| 2.5 | 2.48 | 7.6° |
| 2 | 2.04 | 9.1° |
| 1.5 | 1.49 | 12.7° |
| 1 | 1.00 | 19.1° |

6. Lens according to claim 4, characterized in that the constants c and ψ have, depending on the value of C, the values given in the table below at ±0.125 diopter (D) for C+c, and at ±1° for ψ:

| C (D) | C + c (D) | ψ (°) |
|---|---|---|
| 3 | 2.99 | 4.7° |
| 2.5 | 2.50 | 5.7° |
| 2 | 1.98 | 7.2° |
| 1.5 | 1.49 | 9.5° |
| 1 | 0.99 | 14.4° |

7. Lens according to claim 4, characterized in that the constant c is equal to zero and in that the constant ψ takes on the value given by the formula below at ±1°:

$$\psi = \frac{114}{C.DP}$$

in which formula DP is the pupil diameter expressed in millimeter (mm), ψ being expressed in degrees (°) and C in diopters (D).

8. Lens according to claim 3, characterized in that the optical path $\delta_A(h,\theta)$ satisfies the equation:

$$\delta_A(h, \theta) = \frac{C+c}{2} h^2 \sin^2(\theta - \phi + \eta)$$

in which equation π is equal to ψ for θ−φ between 0° and 90°, and for θ−φ between 180° and 270°, and equal to −ψ for θ−φ between 90° and 180°, and for θ−φ between 270° and 360°, and ψ being predetermined constants.

9. Lens according to claim 8, characterized in that the constants c and ψ have, depending on the values of C, the values given in the table below at ±0.125 diopter (D) for C+c and at ±1°C. for ψ:

| C (D) | C + c (D) | ψ (°) |
|---|---|---|
| 3 | 2.98 | 5.0 |
| 2.5 | 2.47 | 6.1 |
| 2 | 2.00 | 7.4 |
| 1.5 | 1.47 | 10.5 |
| 1 | 0.95 | 16.7 |

10. Lens according to claim 8, characterized in that the constants c and ψ have, depending on the value of C, the values given in the table below at ±0.125 diopter (D) for C+c and at ±1°C. for ψ:

| C (D) | C + c (D) | ψ (°) |
|---|---|---|
| 3 | 3.00 | 3.6 |
| 2.5 | 2.48 | 4.5 |
| 2 | 1.98 | 5.7 |
| 1.5 | 1.49 | 7.5 |
| 1 | 0.97 | 12.0 |

11. Lens according to claim 8, characterized in that the constant c is equal to zero and in that the constant ψ takes on the value given by the formula below at ±1°:

$$\psi = \frac{90}{C.DP}$$

in which formula DP is the pupil diameter expressed in millimeters (mm), ψ being expressed in degrees (0) and C in diopters (D).

12. Lens according to claim 1, characterized in that the term $\delta_A(h,\theta)$ satisfies the equation:

$$\delta_A(h, \theta) = \sum_{i \in E} \beta_i(h) \cos[i(\theta - \phi)]$$

in which equation:

E is a finite set comprising the whole numbers starting from 0; and $\beta_i(h)$ is a set of functions satisfying the following condition:

$$\sum_{i \in E'} \left[ \left( \frac{1}{h_{max} - h_{min}} \int_{h_{min}}^{h_{max}} \frac{2\beta_i(h)}{h^2} dh \right)^2 \right] \geq 0.005 \text{ m}^{-2}$$

in which inequation E' is equal to E disqualifying 0 and 2, while $h_{min}$ and $h_{max}$ are the minimum distance and the maximum distance, respectively, with regard to the optical axis (2) of the zone of the correcting portion (5) provided to correct the astigmatism.

13. Lens according to claim 12, characterized in that each one of the functions $\beta_i(h)$ satisfies the equation:

$$\beta_i(h) = \frac{h^2}{2} \alpha_i$$

in which equation each $\alpha_i$, for i ∈ E, is a constant coefficient.

14. Lens according to claim 13, characterized in that the set E comprises the whole numbers from 0 to 10 and in that the coefficients $\alpha_i$ have, as a function of C, values such that they satisfy the inequation:

$$\sqrt{\sum_{i \in E} (\alpha_i - \alpha_i')^2} \leq 0.05 \text{ m}^{-1}$$

the coefficients $\alpha_i'$ having the values given in the table below:

| $C_{(D)}$ | $\alpha'_0$ | $\alpha'_1$ | $\alpha'_2$ | $\alpha'_3$ | $\alpha'_4$ | $\alpha'_5$ | $\alpha'_6$ | $\alpha'_7$ | $\alpha'_8$ | $\alpha'_9$ | $\alpha'_{10}$ |
|---|---|---|---|---|---|---|---|---|---|---|---|
| 3 | 1.521 | −0.289 | −1.450 | 0.168 | 0 | 0.040 | 0 | 0.019 | 0 | 0.011 | 0 |
| 2.5 | 1.277 | −0.284 | −1.200 | 0.168 | 0 | 0.041 | 0 | 0.019 | 0 | 0.011 | 0 |
| 2 | 1.034 | −0.299 | −0.942 | 0.165 | 0 | 0.048 | 0 | 0.022 | 0 | 0.010 | 0 |
| 1.5 | 0.775 | −0.273 | −0.661 | 0.163 | 0 | 0.040 | 0 | 0.018 | 0 | 0.011 | 0 |
| 1 | 0.522 | −0.261 | −0.383 | 0.157 | 0 | 0.038 | 0 | 0.018 | 0 | 0.010 | 0 |

15. Lens according to claim 13, characterized in that the set E comprises the whole numbers from 0 to 10 and in that the coefficients $\alpha_i$ have, as a function of C, values such that they satisfy the inequation:

$$\sqrt{\sum_{i \in E}(\alpha_i - \alpha'_i)^2} \leq 0.05 \text{ m}^{-1}$$

the coefficients $\alpha_i'$ having the values given in the table below:

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3 | 1.365 | 0 | −1.471 | 0 | 0.081 | 0 | 0 | 0 | 0.016 | 0 | 0 |
| 2.5 | 1.125 | 0 | −1.231 | 0 | 0.085 | 0 | 0 | 0 | 0.017 | 0 | 0 |
| 2 | 1.846 | 0 | −0.951 | 0 | 0.068 | 0 | 0 | 0 | 0.017 | 0 | 0 |
| 1.5 | 0.593 | 0 | −0.693 | 0 | 0.062 | 0 | 0 | 0 | 0.017 | 0 | 0 |
| 1 | 0.358 | 0 | −0.424 | 0 | 0.076 | 0 | 0 | 0 | 0.017 | 0 | 0 |

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3 | 1.502 | −0.216 | −1.465 | 0.127 | 0 | 0.031 | 0 | 0.014 | 0 | 0.008 | 0 |
| 2.5 | 1.261 | −0.218 | −1.215 | 0.126 | 0 | 0.030 | 0 | 0.014 | 0 | 0.008 | 0 |
| 2 | 1.015 | −0.214 | −0.964 | 0.127 | 0 | 0.031 | 0 | 0.014 | 0 | 0.008 | 0 |
| 1.5 | 0.766 | −0.212 | −0.695 | 0.124 | 0 | 0.030 | 0 | 0.014 | 0 | 0.008 | 0 |
| 1 | 0.516 | −0.203 | −0.425 | 0.121 | 0 | 0.030 | 0 | 0.014 | 0 | 0.008 | 0 |

16. Lens according to claim 13, characterized in that the set E comprises the whole numbers from 0 to 10 and in that the coefficients $\alpha_i$ have, as a function of C, values such that they satisfy the inequation:

$$\sqrt{\sum_{i \in E}(\alpha_i - \alpha'_i)^2} \leq 0.05 \text{ m}^{-1}$$

the coefficients $\alpha_i'$ having the values given in the table below:

| $C_{(D)}$ | $\alpha_0$ | $\alpha_1$ | $\alpha_2$ | $\alpha_3$ | $\alpha_4$ | $\alpha_5$ | $\alpha_6$ | $\alpha_7$ | $\alpha_8$ | $\alpha_9$ | $\alpha_{10}$ |
|---|---|---|---|---|---|---|---|---|---|---|---|
| 3 | 1.331 | 0 | −1.472 | 0 | 0.114 | 0 | 0 | 0 | 0.023 | 0 | 0 |
| 2.5 | 1.071 | 0 | −1.206 | 0 | 0.107 | 0 | 0 | 0 | 0.024 | 0 | 0 |
| 2 | 1.830 | 0 | −0.940 | 0 | 0.112 | 0 | 0 | 0 | 0.023 | 0 | 0 |
| 1.5 | 0.575 | 0 | −0.667 | 0 | 0.108 | 0 | 0 | 0 | 0.024 | 0 | 0 |
| 1 | 0.332 | 0 | −0.384 | 0 | 0.105 | 0 | 0 | 0 | 0.025 | 0 | 0 |

17. Lens according to claim 13, characterized in that the set E comprises the whole numbers from 0 to 10, and in that the coefficients $\alpha_i$ have, as a function of C, values such that they satisfy the inequation:

$$\sqrt{\sum_{i \in E}(\alpha_i - \alpha'_i)^2} \leq 0.05 \text{ m}^{-1}$$

the coefficients $\alpha_i'$ having the values given in the table below:

18. Lens according to claim 12, characterized in that each of the functions $\beta_i(h)$ satisfies the equation:

$$\beta_i(h) = \frac{h^2}{2} \alpha_{i,j}$$

in which equation j is a whole number which varies as a function of h by stages, and each $\alpha_i$, regardless of what i and j are, is a predetermined constant coefficient.

19. Lens according to claim 12, characterized in that each one of the functions $\beta_i(h)$ satisfies the equation:

$$\beta_i(h) = \frac{h^2}{2} \sum_{j=0}^{M} \alpha_{i,j} h^j$$

in which equation M is a predetermined whole number and each $\alpha_{ij}$, regardless of what i and j are, is a predetermined constant coefficient.

20. Lens according to claim 1, characterized in that it introduces, in total, an optical path $\delta(h,\theta)$ satisfying, at least for h located between 0.4 mm and 2.4 mm, the equation:

$$\delta(h,\theta) = \delta_o + \delta_A(h,\theta)$$

in which equation $\delta_o$ is an arbitrary constant.

21. Lens according to claim 1, characterized in that it introduces, in total, an optical path $\delta_{inf}(h,\theta)$ satisfying, at least for h located between 0.4 mm and 2.4 mm, the inequation:

$$\delta_{inf}(h,\theta) \leq \delta(h,\theta) \leq \delta_{sup}(h,\theta)$$

$\delta_{inf}(h,\theta)$ and $\delta_{sup}(h,\theta)$ satisfying respectively the following equations:

$\delta_{inf}(h,\theta)=\delta_o+\delta_s(h)+\delta_p(h)+\delta_A(h,\theta)-0.09h^2$ $\delta_{sup}(h,\theta)=\delta_{inf}(h,\theta)+0,18h^2$ in which equations, h and all the δ are expressed in meters (m):

$\delta_s(h)$ is, in the case of spherical correction, the optical path provided for this correction, satisfying the equation:

$$\delta_S(h) = \frac{P_{VL}}{2}h^2$$

in which equation $P_{VL}$ is the spherical power required in order to correct the myopia or hyperopia of said eye, expressed in diopters (D);

$\delta_P(h)$ is, in the case of progressive simultaneous vision correction, the optical path provided for this correction, satisfying the equation:

$$\delta_P(h) = \sum_{k=0}^{k=9} \frac{\gamma_{2k}}{2k+2} 10^{6k} h^{2k+2}$$

the series of coefficients $\gamma_{2k}$ being defined by the respective one of the nine lists SA, SB, SC, MA, MB, MC, LA, LB, LC of coefficients given below:

| k | SA | SB | SC |
|---|---|---|---|
| 0 | 1.398800E + 00 | 3.093330E + 00 | 4.605640E + 00 |
| 1 | −2.160020E + 00 | −4.751140E + 00 | −5.235240E + 00 |
| 2 | 1.337720E + 00 | 2.913640E + 00 | 2.458240E + 00 |
| 3 | −4.327890E − 01 | −9.378340E − 01 | −6.301520E − 01 |
| 4 | 8.154230E − 02 | 1.764900E − 01 | 9.787570E − 02 |
| 5 | −9.410290E − 03 | −2.038990E − 02 | −9.616130E − 03 |
| 6 | 6.736380E − 04 | 1.462890E − 03 | 6.012020E − 04 |
| 7 | −2.914960E − 05 | −6.347570E − 05 | −2.318560E − 05 |
| 8 | 6.978470E − 07 | 1.520000E − 06 | 5.030000E − 07 |
| 9 | −7.091930E − 09 | −1.550000E − 08 | −4.690000E − 09 |

| k | MA | MB | MC |
|---|---|---|---|
| 0 | 1.799020E + 00 | 3.048790E + 00 | 4.144890E + 00 |
| 1 | −1.823880E + 00 | −3.424400E + 00 | −4.233760E + 00 |
| 2 | 8.133470E − 01 | 1.714210E + 00 | 1.949870E + 00 |
| 3 | −2.057150E − 01 | −4.850380E − 01 | −5.212190E − 01 |
| 4 | 3.222470E − 02 | 8.400400E − 02 | 8.739800E − 02 |
| 5 | −3.231690E − 03 | −9.184070E − 03 | −9.410210E − 03 |
| 6 | 2.075120E − 04 | 6.343800E − 04 | 6.468110E − 04 |
| 7 | −8.241900E − 06 | −2.679260E − 05 | −2.734250E − 05 |
| 8 | 1.842050E − 07 | 6.310000E − 07 | 6.460000E − 07 |
| 9 | −1.770040E − 09 | −6.330000E − 09 | −6.520000E − 09 |

| k | LA | LB | LC |
|---|---|---|---|
| 0 | 1.258120E + 00 | 2.3409009E + 00 | 2.660000E + 00 |
| 1 | 2.766510E − 01 | −1.6016233E + 00 | −3.029760E + 00 |
| 2 | −5.863900E − 01 | 8.5580090E − 01 | 1.837520E + 00 |
| 3 | 2.158210E − 01 | −4.0855924E − 01 | −6.361990E − 01 |
| 4 | −3.890640E − 02 | 1.2233248E − 01 | 1.293960E − 01 |
| 5 | 4.063430E − 03 | −2.1406740E − 02 | −1.595350E − 02 |
| 6 | −2.578890E − 04 | 2.2148862E − 03 | 1.205290E − 03 |
| 7 | 9.821560E − 06 | −1.3380186E − 04 | −5.450000E − 05 |
| 8 | −2.065710E − 07 | 4.3658573E − 06 | 1.350000E − 06 |
| 9 | 1.845210E − 09 | −5.9468409E − 08 | −1.410000E − 08 |

22. Lens according to claim 1, characterized in that it introduces, in total, an optical path $\delta(h,\theta)$ satisfying, at least for h located between 0.4 mm and 2.4 mm, the inequation:

$\delta_{inf}(h,\theta) \leq \delta(h,\theta) \leq \delta_{sup}(h,\theta)$ $\delta_{inf}(h,\theta)$ and $\delta_{sup}(h,\theta)$ satisfying respectively the following equations:

$\delta_{inf}(h,\theta)=\delta_o+\delta_s(h)+\delta_p(h)+\delta_A(h,\theta)-0.09h^2$ $\delta_{sup}(h,\theta)=(h,\theta)+0,18h^2$ in which equations, h and all the δ are expressed in meters (m):

$\delta_s(h)$ is, in the case of spherical correction, the optical path provided for this correction, satisfying the equation:

$$\delta_S(h) = \frac{P_{VL}}{2}h^2$$

in which equation $P_{VL}$ is the spherical power required to correct the myopia or hyperopia of said eye, expressed in diopters (D);

$\delta_P(h)$ is, in the case of progressive simultaneous vision correction, the optical path provided for this correction, satisfying the equation:

$$\delta_P(h) = \frac{P_{ADD}}{2}h^2 - \sum_{k=0}^{k=9} \frac{\gamma_{2k}}{2k+2} 10^{6k} h^{2K+2}$$

where $P_{ADD}$ is the addition required for the wearer of the lens for near vision, expressed in diopters (D), the series of coefficients $\gamma_{2k}$ being defined by the respective one of the nine lists SA, SB, SC, MA, MB, MC, LA, LB, LC given below:

| k | SA | SB | SC |
|---|---|---|---|
| 0 | 1.398800E + 00 | 3.093330E + 00 | 4.605640E + 00 |
| 1 | −2.160020E + 00 | −4.751140E + 00 | −5.235240E + 00 |
| 2 | 1.337720E + 00 | 2.913640E + 00 | 2.458240E + 00 |
| 3 | −4.327890E − 01 | −9.378340E − 01 | −6.301520E − 01 |
| 4 | 8.154230E − 02 | 1.764900E − 01 | 9.787570E − 02 |
| 5 | −9.410290E − 03 | −2.038990E − 02 | −9.616130E − 03 |
| 6 | 6.736380E − 04 | 1.462890E − 03 | 6.012020E − 04 |
| 7 | −2.914960E − 05 | −6.347570E − 05 | −2.318560E − 05 |
| 8 | 6.978470E − 07 | 1.520000E − 06 | 5.030000E − 07 |
| 9 | −7.091930E − 09 | −1.550000E − 08 | −4.690000E − 09 |

| k | MA | MB | MC |
|---|---|---|---|
| 0 | 1.799020E + 00 | 3.048790E + 00 | 4.144890E + 00 |
| 1 | −1.823880E + 00 | −3.424400E + 00 | −4.233760E + 00 |
| 2 | 8.133470E − 01 | 1.714210E + 00 | 1.949870E + 00 |
| 3 | −2.057150E − 01 | −4.850380E − 01 | −5.212190E − 01 |
| 4 | 3.222470E − 02 | 8.400400E − 02 | 8.739800E − 02 |
| 5 | −3.231690E − 03 | −9.184070E − 03 | −9.410210E − 03 |
| 6 | 2.075120E − 04 | 6.343800E − 04 | 6.468110E − 04 |
| 7 | −8.241900E − 06 | −2.679260E − 05 | −2.734250E − 05 |
| 8 | 1.842050E − 07 | 6.310000E − 07 | 6.460000E − 07 |
| 9 | −1.770040E − 09 | −6.330000E − 09 | −6.520000E − 09 |

| k | LA | LB | LC |
|---|---|---|---|
| 0 | 1.258120E + 00 | 2.3409009E + 00 | 2.660000E + 00 |
| 1 | 2.766510E − 01 | −1.6016233E + 00 | −3.029760E + 00 |
| 2 | −5.863900E − 01 | 8.5580090E − 01 | 1.837520E + 00 |
| 3 | 2.158210E − 01 | −4.0855924E − 01 | −6.361990E − 01 |

-continued

| 4 | −3.890640E − 02 | 1.2233248E − 01 | 1.293960E − 01 |
| 5 | 4.063430E − 03 | −2.1406740E − 02 | −1.595350E − 02 |
| 6 | −2.578890E − 04 | 2.2148862E − 03 | 1.205290E − 03 |
| 7 | 9.821560E − 06 | −1.3380186E − 04 | −5.450000E − 05 |
| 8 | −2.065710E − 07 | 4.3658573E − 06 | 1.350000E − 06 |
| 9 | 1.845210E − 09 | −5.9468409E − 08 | −1.410000E − 08 |

23. Method for the preparation of a contact or intraocular lens according to claim 1, characterized in that it comprises:
 a) a step of determination of the optical path that must be introduced by the correcting portion of this lens;
 b) a step of selection of the shape of the posterior surface of said correcting portion from a series of predetermined shapes, in order to procure optimal comfort for the wearer of the lens;
 c) a step of determination of the shape of the anterior surface of said correcting portion, starting from said shape selected for the posterior surface in step b) and from the optical path determined in step a); and
 d) a step of manufacturing said lens with the correcting portion presenting the anterior surface and the posterior surface thus determined.

24. Method for the preparation of a contact or intraocular lens according to claim 1, characterized in that it comprises:
 a) a step of determination of the optical path that must be introduced by the correcting portion of this lens;
 b) a step of selection of the shape of the anterior surface of said correcting portion from a series of predetermined shapes;
 c) a step of determination of the shape of the posterior surface of said correcting portion, starting from said shape selected for the anterior surface in step b) and from the optical path determined in step a);
 d) a step of manufacturing said lens with said correcting portion presenting said posterior surface and anterior surface thus determined.

25. A contact or intraocular lens comprising a portion for correcting the vision of an astigmatic eye, the lens defining an optical axis and a reference meridian line perpendicular thereto, the lens further having a generally convex anterior face and a generally concave posterior face, wherein one of the anterior or posterior faces is shaped so as to correct for astigmatism in that an optical path through the correcting portion of the lens varies as a function of the angular separation from the reference meridian line, and wherein the correcting portion is divided into at least two sectors having different astigmatism correction axes, the lens further having an angular misalignment tolerance that is increased by at least about 30% over a standard toric lens of the same class.

26. The lens of claim 25, wherein the correcting portion is defined generally within a circle about the optical axis having a radius between about 0.4 mm and 2.4 mm.

27. The lens of claim 25, wherein the two sectors are separated by a line passing through the optical axis and angularly oriented with respect to the reference meridian line by an angle $\phi$, where $\phi$ is the nominal axis required to correct the astigmatism of the eye.

28. The lens of claim 27, wherein each of the two sectors has an astigmatism correction axis that differs from $\phi$.

29. The lens of claim 28, wherein one of the two sectors has an astigmatism correction axis that is equal to $\phi-\psi$, while the other of the two sectors has an astigmatism correction axis that is equal to $\phi+\psi$, where $\psi$ is non-zero.

30. The lens of claim 25, wherein the correcting portion is divided into four sectors, at least two of which have different astigmatism correction axes.

31. The lens of claim 30, wherein the four sectors are separated by two perpendicular lines intersecting at the optical axis so as to define two pairs of sectors that are diametrically-opposed across the optical axis, one of the lines being angularly oriented with respect to the reference meridian line by an angle $\phi$.

32. The lens of claim 31, wherein each pair of sectors that are diametrically-opposed across the optical axis have equal astigmatism correction axes.

33. The lens of claim 32, wherein two of the sectors have astigmatism correction axes equal to $\phi-\psi$, while the other two sectors have astigmatism correction axes equal to $\phi+\psi$, where $\psi$ is non-zero.

34. A contact or intraocular lens comprising a portion for correcting the vision of an astigmatic eye, the lens having anterior and posterior faces and defining an optical axis and a reference meridian line perpendicular thereto, wherein at least one of the anterior or posterior faces has an non axisymmetric shape that is not purely toric, and wherein the distribution of an optical path through the correcting portion of the lens is the sum of several optical paths that include at least:
 an optical path that characterizes a correction of astigmatism; and
 an optical path that characterizes an non axisymmetric aberration other than astigmatism,
 the lens further having an angular misalignment tolerance that is increased by at least about 30% over a standard toric lens of the same class.

35. The lens of claim 34, wherein only the anterior face is non axisymmetric.

36. The lens of claim 34, wherein only the posterior face is non axisymmetric.

37. The lens of claim 34, wherein both the anterior and posterior faces are non axisymmetric.

38. The lens of claim 34, wherein the optical path through the correcting portion of the lens also corrects for spherical error.

39. The lens of claim 34, wherein the optical path through the correcting portion of the lens also includes a multifocal correction for presbyopia.

40. The lens of claim 34, wherein the optical path through the correcting portion of the lens also includes a progressive power correction for presbyopia.

41. The lens of claim 34, wherein the optical path through the correcting portion of the lens also corrects for a coma-like aberration.

* * * * *

UNITED STATES PATENT AND TRADEMARK OFFICE
CERTIFICATE OF CORRECTION

PATENT NO.   : 6,533,416 B1
DATED        : March 18, 2003
INVENTOR(S)  : Fermigier et al.

It is certified that error appears in the above-identified patent and that said Letters Patent is hereby corrected as shown below:

Column 3,
Line 18, "$\sin^2(\theta - \phi)$" should read -- $\sin^2(\theta - \phi)$, --.
Line 57, "shift $\psi$" should read -- shift $\varphi$ --.
Line 60, "$\psi$" should read -- $\varphi$ --.
Line 63, "$\psi$" should read -- $\varphi$ --.

Column 4,
Line 1, "$\psi$" should read -- $\varphi$ --.
Line 39, "such" should read -- is such --.
Line 42, "$\sin^2(\theta - \phi)$" should read -- $\sin^2(\theta - \phi)$. --.

Column 5,
Line 34, "the a invention" should read -- the invention --.

Column 6,
Line 41, "and at" should read -- and at $\pm 1°$ for $\psi$: --.

Column 7,
Line 49, "6 mm. same" should read -- 6mm. Preferably, for the same --, and "Preferably" should start a new paragraph.
Line 50, "on the n" should read -- on the value of C, the values given --.

Column 8,
Line 25, "0.005 m$^2$" should read -- 0.005 m$^{-2}$ --.

Column 13,
Line 19, "$\Phi$with" should read -- $\Phi$ with --.
Line 45, "ionque" should read -- torique --.
Line 52, "$\Phi$is" should read -- $\Phi$ is --.

Column 14,
Line 39, "ivN" should read -- i$\in$N --.

Column 15,
Line 55, "corresponding. essentially" should read -- corresponding essentially --.

UNITED STATES PATENT AND TRADEMARK OFFICE
CERTIFICATE OF CORRECTION

PATENT NO. : 6,533,416 B1
DATED : March 18, 2003
INVENTOR(S) : Fermigier et al.

It is certified that error appears in the above-identified patent and that said Letters Patent is hereby corrected as shown below:

Column 16,
Line 22, "$\Phi'$]" should read -- $\Phi$] --.

Line 27, " $MTFa[\delta_{torique}(h, \theta - x) - \delta_{torique}(h, \theta)] \geq MTFa\left[0, 25\dfrac{h^2}{2}\right]$ "

should read -- $MTFa\left[\delta_{torique}\oslash(h, 0-x) - \delta_{torique}\oslash(h, 0)\right] \geq MTFa\left[0,25\dfrac{h^2}{2}\right]$ --

Line 37, " $MTFa[\delta_A(h, \theta - x) - \delta_{torique}(h, \theta)] \geq MTFa\left[0, 25\dfrac{h^2}{2}\right]$ "

should read -- $MTFa\left[\delta_A(h, 0-x) - \delta_{torique}\oslash(h, \theta)\right] \geq MTFa\left[0,25\dfrac{h^2}{2}\right]$ --

Column 17,
Line 49, "1.2" should read -- 7.2 --.
Line 55, "0.121" should read -- 0.127 --.
Line 67, "demonstrates the" should read -- demonstrates that the --.

Column 18,
Line 5, "efficient" should read -- coefficient --.
Line 8, "divide" should read -- divided --.

Column 19,
Line 25, "900" should read -- 90° --.

Column 21,
Line 36, "coefficients a," should read -- coefficients $\alpha_i$ --.
Line 39, "periods" should read -- period $\Pi$ --.
Line 45, "a9" should read -- $\alpha_9$ --.
Line 56, "0" should read -- $\theta$ --.

Column 23,
Line 21, "$\alpha_j$" should read -- $\alpha_{ij}$ --.

Column 25,
Line 57, "$\Delta\phi$is" should read -- $\Delta\phi$ is --.

UNITED STATES PATENT AND TRADEMARK OFFICE
CERTIFICATE OF CORRECTION

PATENT NO.   : 6,533,416 B1
DATED         : March 18, 2003
INVENTOR(S) : Fermigier et al.

It is certified that error appears in the above-identified patent and that said Letters Patent is hereby corrected as shown below:

Column 27,
Line 47, ", and" should read -- , c and --.
Line 52, "±1°C. for" should read -- ±1°C for --.
Line 67, "±1°C. for" should read -- ±1°C for --.

Column 30,
Line 61, "$\delta_{inj}(h, \theta)$" should read -- $\delta(h, \theta)$ --.

Signed and Sealed this

Second Day of March, 2004

JON W. DUDAS
*Acting Director of the United States Patent and Trademark Office*